(12) United States Patent
Bao et al.

(10) Patent No.: US 9,175,060 B2
(45) Date of Patent: Nov. 3, 2015

(54) PEG MODIFIED EXENDIN OR EXENDIN ANALOG AND COMPOSITIONS AND USE THEREOF

(75) Inventors: Wenchao Bao, Shanghai (CN); Hongjing Xu, Shanghai (CN); Gang Yu, Shanghai (CN); Yajun Zuo, Shanghai (CN)

(73) Assignee: Shanghai Benemae Pharmaceutical Corporation, Shanghai (CN)

( * ) Notice: Subject to any disclaimer, the term of this patent is extended or adjusted under 35 U.S.C. 154(b) by 882 days.

(21) Appl. No.: 12/514,790

(22) PCT Filed: Nov. 13, 2007

(86) PCT No.: PCT/CN2007/003203
§ 371 (c)(1),
(2), (4) Date: May 13, 2009

(87) PCT Pub. No.: WO2008/058461
PCT Pub. Date: May 22, 2008

(65) Prior Publication Data
US 2010/0240586 A1    Sep. 23, 2010

(30) Foreign Application Priority Data

Nov. 14, 2006  (CN) .......................... 2006 1 0118326
Jul. 23, 2007  (CN) .......................... 2007 1 0138718

(51) Int. Cl.
*A61K 38/26* (2006.01)
*C07K 14/575* (2006.01)
*A61K 47/48* (2006.01)
*A61K 38/00* (2006.01)

(52) U.S. Cl.
CPC ........... *C07K 14/57563* (2013.01); *A61K 38/26* (2013.01); *A61K 47/48215* (2013.01); *A61K 47/48338* (2013.01); *A61K 38/00* (2013.01)

(58) Field of Classification Search
CPC . A61K 47/48215; A61K 38/26; C07K 14/605
See application file for complete search history.

(56) References Cited

U.S. PATENT DOCUMENTS

| 6,566,506 | B2 | 5/2003 | Greenwald et al. |
| 6,872,700 | B1 | 3/2005 | Young et al. |
| 6,924,264 | B1 | 8/2005 | Prickett et al. |
| 7,153,825 | B2 | 12/2006 | Young et al. |
| 2002/0052443 | A1 | 5/2002 | Greenwald et al. |
| 2004/0142866 | A1* | 7/2004 | Sun et al. .......................... 514/12 |
| 2005/0180946 | A1* | 8/2005 | Ji et al. .......................... 424/78.38 |

FOREIGN PATENT DOCUMENTS

| CN | 1363559 | A | 8/2002 |
| CN | 1372570 | A | 10/2002 |
| CN | 1676163 | A | 10/2005 |
| EP | 1496076 | A1 | 1/2005 |
| WO | 98/41562 | A1 | 9/1998 |
| WO | 00/66629 | A1 | 11/2000 |
| WO | 03076490 | A1 | 9/2003 |
| WO | 2004089280 | A2 | 10/2004 |
| WO | 2004/093823 | A2 | 11/2004 |
| WO | 2005/058954 | A1 | 6/2005 |
| WO | 2007047834 | A2 | 4/2007 |

OTHER PUBLICATIONS

International Search Report for International Application No. PCT/CN2007/003203 dated Mar. 6, 2008, 6 pages.
Buse, J.B. et al., "Effects of Exenatide (Exendin-4) on Glycemic Control Over 30 Weeks in Sulfonylurea-Treated Patients With Type 2 Diabetes," Diabetes Care, 2004, 27: 2628-2635.
Tsubery H. et al., "Prolonging the Action of Protein and Peptide Drugs by a Novel Approach of Reversible Polyethylene Glycol Modification," The Journal of Biological Chemistry, 2004, 279 (37): 38118-38124.
Eng, J. et al., "Isolation and Characterization of Exendin-4, an Exendin-3 Analogue, from Heloderma suspectum Venom," The Journal of Biological Chemistry, 1992, 267 (11): 7402-7405.
Eng, J. et al., "Purification and Structure of Exendin-3, a New Pancreatic Secretagogue Isolated from Heloderma horridum Venom" The Journal of Biological Chemistry, 1990, 265 (33): 20259-20262.
Bonner-Weir S. et al., "New Sources of Pancreatic β-cells," Nature Biotechnology, 2005, 23 (7): 857-861.
Ding X. K. et al., "Exendin-4, a Glucagon-Like Protein-1 (GLP-1) Receptor Agonist, Reverses Hepatic Steatosis in ob/ob Mice," Hepatology, 2006, 43 (1): 173-181.
Gong, Q. H. et al., "Recombinant Human Glucagon-Like Peptide-1 (7-36) enhances insulin release and insulin mRNA expression in INS-1 Cells," Chin J Endocrinol Metab, 2004, 20: 559-560.

* cited by examiner

*Primary Examiner* — Christina Bradley
(74) *Attorney, Agent, or Firm* — Perkins Coie LLP; Yingli Wang

(57) ABSTRACT

Exendins or exendin analogs modified by one or more PEG derivatives that may be linked to one or more amino acids of the exendins or exendin analogs are provided. The PEG derivatives may have branched structure set forth in any one of formulas I-IV. Compositions including the PEG derivative modified exendin or exendin analog, methods of making or administering the modified exendin or exendin analog, and various uses thereof are also provided.

11 Claims, 6 Drawing Sheets

PEG MODIFIED EXENDIN OR EXENDIN ANALOG AND COMPOSITIONS AND USE THEREOF

CROSS-REFERENCE TO RELATED APPLICATIONS

The present application is a national stage application of International Application No. PCT/CN2007/003203 filed Nov. 13, 2007, which claims the benefit of Chinese Patent Application No. 200610118326.X filed Nov. 14, 2006 and Chinese Patent Application No. 200710138718.7 filed on Jul. 23, 2007, all of which are incorporated herein by reference in their entirety.

BACKGROUND

Glucagon-like peptide-1 (GLP-1) was first discovered in 1987 and identified as a glucose-dependent intestinal secreted hormone peptide. GLP-1 peptide transmits signals through G protein-coupled receptors (GPCR), and stimulates β islet cells to secret insulin to inhibit glucagon secretion, gastric emptying and gastric acid secretion and effects other physiological functions.

The exendins are peptides (J. Biol. Chem. 1999, 265, 20259-20262; J. Biol. Chem. 1992, 267, 7402-7405) found in the salivary secretions of venomous lizards the Gila monster and *Heloderma horridum*. These exendins, as represented by exendin-4, are highly homologous to GLP-1 [7-36]. Previous researches have discovered that the exendins can bind to GLP-1 receptors and exert similar pharmacological effects, such as stimulating insulin secretion, effectively controlling blood sugar levels after a meal, reducing the glycosylation level of hemoglobin and inhibiting gastric emptying. Testing on animals found that long term use of GLP-1 receptor peptides can effectively reduce the resistance to insulin which may lead to the reversion of diabetes mellitus deterioration. Additionally, it has been found that a number of insulinotropic agonists such as GLP-1 and exendin-4 can stimulate regeneration of β islet cells (Nat. Biotech. 2005, 23, 857-861) and ameliorate nonalcoholic fatty livers (Hepatology 2006, 43, 173-181). These discoveries make such peptides a hot area in the studies of diabetes and adiposis. Wu Dengxi and Sun Yukun (Chinese patent: ZL01112856) have modified exendin-4 and obtained a series of exendin-4 analogs with the same functions as the native exendin-4. Recently, a new exendin based drug, exendin-4 (Byetta®), came into the US market. This drug was jointly developed by Amylin and Eli Lilly and requires two injections per day. The drug has drawn attention in the therapeutic field of diabetes and adiposis. However, clinical researches discovered that about 41% of the patients produced antibodies against exendin-4 after 30 weeks of treating with such drug (Diabetes Care. 2004, 27, 2628-2635).

Protein/peptide drugs typically have shortcomings such as a short half life in blood, poor physical and chemical stability, and prone to in vivo degradation by proteases. As a result, multiple injections of such drugs are required every day, causing lots of pain and inconvenience to patients. How to extend the half life of these drugs has puzzled the biotechnology industry for a long time. Presently, no one has found a universally acceptable solution to this problem.

PEG modification technology emerged in the 1970s and was applied in the technology of making protein/peptide drugs. When certain protein/peptides were modified by linear or branched PEG, the modification may have given the following features to the protein/peptide: (1) an improvement in physical and chemical stability; (2) a decrease in immunogenicity; (3) an increase in resistance to protease degradation; (4) an extension of half life in blood due to the increase in PEG molecular weight leading to reduced kidney clearance; and (5) an improvement in drug solubility and cell membrane penetration. According to studies by A. Yang and K. Precourt, exendin-4 is primarily metabolized through kidney clearance. Therefore, they employed a PEG having a molecular weight in the range of 500 to 20,000 Da to modify exendins (Chinese patent: CN1372570A) to reduce the effect of kidney clearance.

However, a main defect of the PEG technology is that the bioactivity of a modified drug generally drops significantly after the modification. Haim Tsubery et. al. employed 9-hydroxymethyl-7-sulfofluorene-N-hydroxysuccinimide (FMS) to activate PEG to be coupled with exendin-4, and then the PEG groups were released from the exendin-4 by in vivo hydrolysis. Thus the bioactivity of exendin-4 was restored. Although this method provides a solution to the problem of low bioactivity due to PEG modification, un-modified exendin-4 was released after in vivo hydrolysis and the problem of immunogenicity resulting from frequent injections has remained unsolved (J. Biol. Chem. 2004, 279, 38118-38124).

Existing defects of known exendins and exendin analogs include short time intervals between doses, the production of antibodies in patients from long-term injection, and the reduction of bioactivity after modification with PEG. These defects make it hard for exendins and exendin analogs to be applied in practice and require the administration of large dosages of exendins or exendin analogs which severely impedes the application of exendin technology.

SUMMARY

In certain embodiments, exendin or exendin analogs modified by one or more polyethylene glycol (PEG) molecules or derivatives are provided. In certain embodiments, PEG modified exendins or exendin analogs having one or more PEG derivatives linked to one or more amino acids of the exendins or exendin analogs or derivatives are provided. The PEG derivatives may have linear or branched structures. In certain embodiments, the PEG derivatives may have a branched structure, e.g., as set forth in any one of Formulas (I-IV) described herein. In certain embodiments, compositions including a PEG modified exendin or exendin analog, methods of making or administering such modified exendins or exendin analogs, and various uses thereof, e.g., for treatment of diabetes, are provided. The PEG modified exendins or exendin analogs exhibit improved and unexpected properties and characteristics, such as, for example, long half life in blood, high bioactivity, and/or low immunogenicity.

DETAILED DESCRIPTION

PEG Modification

Figure 1:
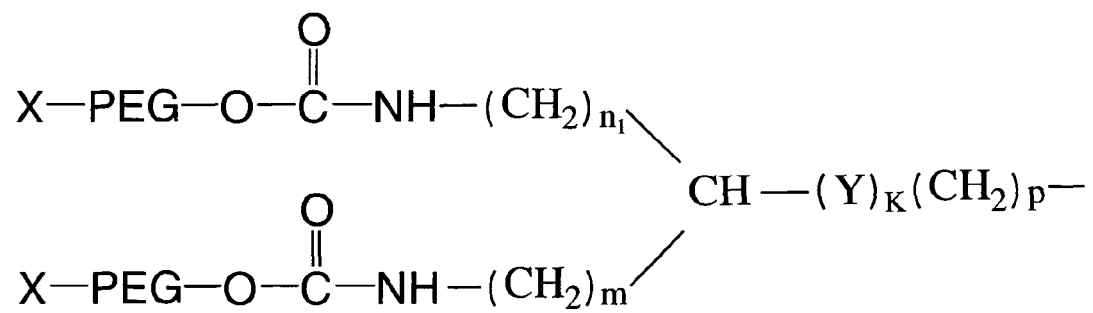
FIG. 1 is the structure of Formula I of branched PEG derivatives.
Figure 2:
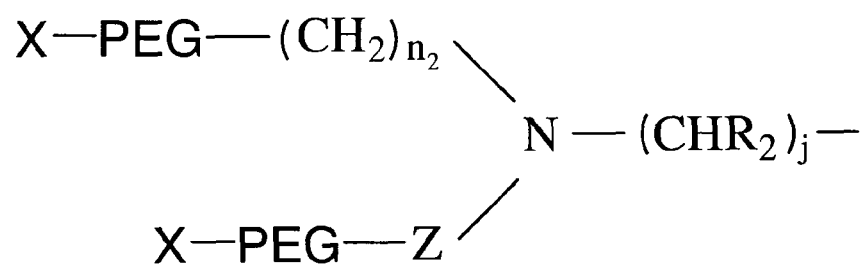
FIG. 2 is the structure of Formula III of branched PEG derivatives.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In certain embodiments, exendins or exendin analogs modified by one or more PEG derivatives are provided. In certain embodiments, novel PEG modifications of exendins and/or exendin analogs are employed to make PEG modified exendins or exendin analogs which exhibit improved and unexpected properties and characteristics, such as, for example, long half life in blood, high bioactivity, and/or low immunogenicity.

Different chemical structures of PEG derivatives may have different effects on the bioactivity of the peptides modified by such PEG derivatives or molecules. PEG derivatives may have linear or branched structures. The branched structures include, e.g., double branched-chains as well as multiple branched-chains. The PEG derivatives having double branched-chains include, for example, without limitation, the structures set forth in Formulas I, II, III and IV below.

In certain embodiments, the branched PEG derivatives may include, for example, without limitation, the structure set forth in Formula I below:

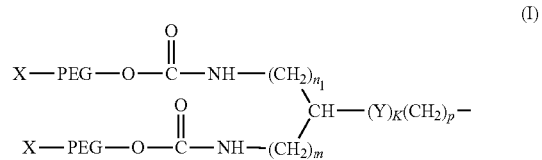

Wherein, X is hydrogen or a protecting group. The protecting group may be any group which can react with a free hydroxyl group of the PEG derivative, and at the same time can prevent its further reaction with other groups. Examples of protecting groups include, for example, without limitation, alkyl groups such as methyl, dimethyl, ethyl, propyl, and isopropyl.

Furthermore, PEG is —O(CH$_2$CH$_2$O)$_q$—, q is a positive integer; n$_1$ is an integer from 0-5; m is an integer from 0-5; Y is O, S, SO, SO$_2$ or NR$_1$, wherein R$_1$ is hydrogen or substituted or unsubstituted (C$_1$-C$_8$) alkyl group or substituted or unsubstituted cycloalkyl group; k is 0 or 1; and p is an integer from 0-6. A PEG having the structure set forth in Formula I can be synthesized by conventional chemical methods. For example, a synthesis method for PEG having the structure set forth in Formula I is described in U.S. Pat. No. 6,566,506.

In certain embodiments, a PEG derivative used herein which comprises the branched structure of Formula I has the specific structure set forth in Formula II below:

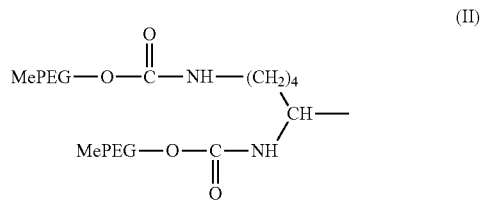

Wherein, PEG is —O(CH$_2$CH$_2$O)$_q$—, q is a positive integer, and Me is a methyl group.

In certain embodiments, a branched-chain PEG derivative has the structure of Formula III below:

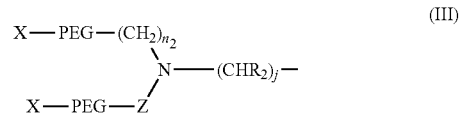

Wherein, X is hydrogen or a protecting group; PEG is —O(CH$_2$CH$_2$O)$_q$—, q is a positive integer; n$_2$ is an integer from 0-10; Z is: (CH$_2$)$_i$, (CH$_2$)$_i$OCO, (CH$_2$)$_i$NHCO, or (CH$_2$)$_i$CO, wherein i is an integer from 0-10; R$_2$ is hydrogen, substituted or unsubstituted (C$_1$-C$_{12}$) alkyl group, substituted aryl, aralkyl or heteroalkyl group; and j is an integer from 1-12. The above mentioned PEG derivative structure of Formula III can be synthesized by conventional chemical methods, one of which is provided in the Chinese Patent No. ZL03801105.0.

In certain embodiments, a PEG derivative used herein which comprises the branched structure of Formula III has the structure set forth in Formula IV below:

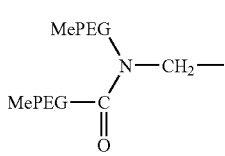

(IV)

Wherein, PEG is —O(CH$_2$CH$_2$O)$_q$, q is a positive integer, and Me is a methyl group.

The molecular weights of PEG derivatives may affect the bioactivity of PEG modified peptides. In certain embodiments, the molecular weight of the linear or branched PEG derivative used is about 200 Da or higher. Preferably the molecular weight is about 5,000 Da or higher or about 20,000 Da or higher. In certain embodiments, the molecular weight of PEG derivative used is in the range of about 5,000 Da to about 50,000 Da. Preferably, the molecular weight of the PEG derivative used is in the range of 20,000 Da to 50,000 Da, or 20,000 Da to 45,000 Da, or 20,000 Da to 40,000 Da. The molecular weights of PEG derivatives referred to herein are the number average molecular weights (Mn) measured by the method of Gel Permeation Chromatography (GPC) unless otherwise specified (Dong Yanming, Guidebook of Macromolecule Analysis, Beijing, China Petrochemical Press, 2004, 416-427). PEG derivatives with different molecular weights can either be purchased from commercial providers, or synthesized using conventional methods known in the relevant technical field.

In certain embodiments, the PEG derivatives have branched structures with molecular weights higher than 20,000 Da. Preferably, the molecular weights of the branched PEG derivatives used are in the range of higher than 20,000 Da to about 50,000 Da, or higher than 20,000 Da to about 45,000 Da, or higher than 20,000 Da to about 40,000 Da.

The PEG modification of exendins or exendin analogs is achieved by linking the activated PEG derivatives to side chain of an amino acid residue or the N-terminus or C-terminus of amino acids of the exendins or exendin analogs. For example, PEG derivatives containing different activation groups can bind to different side chains, the N-terminus or C-terminus of amino acids, or to a specific amino acid. Amino acid groups that can be chemically bound to activated PEG derivatives include but are not limited to the N-terminus α-amino groups, the lysine residue side chain ε-amino groups, imino groups on histidine residue side chain imidazolyl group of peptides, the carboxyl terminal of peptides, side chain carboxyl groups of aspartic acid and glutamic acid, side chain hydroxyl groups of serine and threonine, side chain mercapto groups of cysteine, etc. In general, such chemical binding is achieved through electrophilic and nucleophilic reactions. For example, the linkage of PEG derivatives activated by N-hydroxyl succinimide to α-amino groups of N-terminus, lysine side chain ε-amino groups and free amino groups such as imino groups on histidine side chain imidazolyl groups are created through such reactions. Additionally, PEGs containing aldehyde activation groups can be specifically linked to the N-terminus of peptides by reductive alkylation. Indeed, methods of linking PEG derivatives to exendins or exendin analogs by using various activation groups, and the PEG modified exendins or exendin analogs produced thereof are provided in certain embodiments. PEG derivatives with various activation groups can be purchased from commercial providers, or synthesized using conventional methods known in the relevant technical field.

In certain embodiments, exendins or exendin analogs coupled with one or more PEG derivatives are provided where the number of PEG derivatives coupled to the exendins or exendin analogs is dependent upon the number of free radical groups on the exendins or exendin analogs, the activation groups of PEG derivative, and/or the PEG derivative's molecular weight. Generally, the more free radical groups that the exendins or exendin analogs have, the more PEG derivatives will be linked thereto. Also generally, the larger the activated PEG derivative's molecular weight is, the less PEG derivative will be linked to the peptides. In certain embodiments, the exendins or exendin analogs are modified by one, two, three or four PEG derivatives. Preferably, an exendin or exendin analog is modified by one or two PEG derivatives.

Mixtures generated by binding PEG derivatives to exendins or exendin analogs can be effectively separated by conventional means, for example, ion exchange separation, gel filtration separation, or reversion phase chromatography. The ion exchange chromatography may include anion and cation exchange chromatography. Different ion exchange methods may have different effects on the separation and purification results. Since different exendins or exendin analogs have different numbers and kinds of amino acids, and thus have different molecular weights, the ultimate molecular weights of exendins or exendin analogs modified by PEG derivatives are the total molecular weights of the PEG derivatives and the exendins or exendin analogs. After the processes of separation, purification and buffer solution substitution, the PEG modified exendins or exendin analogs may be further processed to make pharmaceutical compositions.

Exendins or Exendin Analogs

Exendins or exendin analogs herein refer to peptides or peptide derivatives having an amino acid sequence homologous or identical to a portion or the entire sequence of native exendins. Exendins or exendin analogs can bind to GLP-1 receptors and stimulate a cascade of cell signal transmissions. Such peptides can be obtained through solid phase chemical synthesis or genetic engineering, followed by separation and purification.

Exendins or exendin analogs herein include but are not limited to the native exendin-3 and exendin-4. The native exendin-3 has the following amino acid sequence:

(SEQ ID NO: 1)
[His-Ser-Asp-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-OH].

The native exendin-4 has the following amino acid sequence:

(SEQ ID NO: 2)
[His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-NH$_2$].

In certain embodiments, the exendins or exendin analogs include but are not limited to the peptide analogs obtained by amino acid substitutions, additions or deletions of the native exendin-3 and exendin-4 amino acid sequences. The amino acids substitutions of Exendin-3 and Exendin-4 include substitutions with natural amino acids as well as unnatural amino acids. Unnatural amino acids include but are not limited to azetidinecarboxylic acid, 2-amino-hexanedioic acid, 3-amino-hexanedioic acid, β-lactamic acid, aminopropionic acid, 2-aminobutanoic acid, 4-aminobutanoic acid, 6-aminohexanoic acid, 2-aminoheptanoic acid, 2-amino-2-methylpropanoic acid, 3-amino-2-methylpropanoic acid, 2-aminoheptanedioic acid, 2-amino-3,3-dimethylbutanoic acid, desmonsine, 2,2-diaminoheptanedioic acid, 2,3-diaminopropanoic acid, N-ethylglycine, N-ethylasparagine, homoproline, hydroxylysine, allo-hydroxylysine, 3-hydroxyproline, 4-hydroxyproline, isodesmonsine, alloisoleucine, N-methylalanine, N-methylglycine, N-methylisoleucine, N,N-methylpentylglycine, N-methylvaline, naphthalanine, norvaline, norleucine, ornithine, pentylglycine, pipecolic acid and thioproline. Preferentially, exendin analogs include one, two, three, four or five amino acid substitutions.

In certain embodiments, the exendin analogs include peptide analogs obtained by adding or subtracting one or more amino acids to or from the native exendin-3 or exendin-4 amino acid sequences. Preferably, the exendin analogs include peptide analogs obtained by adding or removing one to twenty amino acids to or from the native exendin-3 or exendin-4 amino acid sequences. In certain embodiments, the exendin analogs include peptide analogs obtained by adding or removing one to fifteen amino acids to or from the native exendin-3 or exendin-4 amino acid sequences or by adding or removing one to ten amino acids to or from the native exendin-3 or exendin-4 amino acid sequences or by adding or removing one to nine amino acids to or from the native exendin-3 or exendin-4 amino acid sequences.

Exendin analogs may have reversible or irreversible chemical blocking or modification on their N-terminus, C-terminus, or side chains. For example, the C-terminus of an exendin or exendin analog may be amidated.

In certain embodiments, the exendins or exendin analogs comprise amino acid sequences of SEQ ID NOs: 1-265. Preferably, exendins or exendin analogs comprise amino acid sequences of SEQ ID NOs: 1-2 or amino acid sequences of SEQ ID NOs: 3-229 or amino acid sequences of SEQ ID NOs: 230-265.

The activity of PEG modified exendins or exendin analogs described herein can be tested at the cell level according to the assay published by Gong Qiuhong et. al. (Chinese Journal of Incretion and Metaboly, 2004, 20, 559-560). Briefly, the assay is conducted by adding glucose and PEG modified exendins or exendin analogs of various concentrations to INS-1 cells, incubating for 4 hours, detecting the amount of insulin in the supernatant using radioimmunoassay and finally analyzing the amount of insulin in INS-1 cells using RT-PCR technology in a semi-quantitative assay. By using the aforesaid method, large scale screening of the activity of PEG derivative modified exendins or exendin analogs can be achieved. Such screening can also be achieved by testing the change in blood sugar levels in a mouse (e.g. C57 or db/db mouse) at different time points after doses.

Pharmaceutical Compositions and Uses Thereof

In certain embodiments, pharmaceutical compositions or compounds including PEG modified exendins or exendin analogs as described herein are provided. The PEG derivative modified exendins or exendin analogs described herein may react with various inorganic and organic acids or alkali to form salt. Such salts include salts prepared with organic and inorganic acids, wherein the organic and inorganic acids include but are not limited to hydrochloric acid, hydrobromic acid, sulfuric acid, phosphoric acid, trifluoroacetic acid, acetic acid, formic acid, methanesulfonic acid, toluenesulfonic acid, maleic acid, fumaric acid and camphorsulfonic acid. Salts prepared with alkali include but are not limited to ammonium salts, alkali metal salts (e.g., sodium and potassium salts), and alkali earth metal salts, (e.g. calcium and magnesium salts). Preferred salts include, e.g., acetate salts, hydrochloride salts and trifluoroacetic salts. The salts may be prepared by conventional methods. For example, such salts may be prepared by reacting the exendins or exendin analogs with one or more equivalents of the appropriate acid or alkali in a solvent or medium in which the resulting salt is insoluble or in a solvent such as water, that is removable by vacuum or by freeze-drying, or by exchanging the ions of an existing salt for another ion on a suitable ion exchange resin.

In certain embodiments, PEG modified exendins or exendin analogs as described herein can also be prepared as pharmaceutically acceptable salts (e.g., salt resulting from an addition reaction of acid) and/or complexes thereof. The preparation of such salts can facilitate the pharmacological use by altering the physical or chemical characteristics of a composition without preventing the composition from exerting its physiological effect. Examples of useful alterations in physical properties include lowering the melting point to facilitate transmucosal administration or increasing the solubility to facilitate the administration of higher concentrations of the drug.

Pharmaceutically acceptable salts include, for example, acid addition salts such as those containing sulfate, hydrochloride, phosophate, sulfamate, acetate, citrate, lactate, tartrate, methanesulfonate, ethanesulfonate, benzenesulfonate, p-toluenesulfonate, cyclohexylsulfamate and quinate salts. Pharmaceutically acceptable salts can also be prepared with various organic and inorganic acids such as, e.g., hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinate. Such salts may be prepared by reacting the exendins or exendin analogs with one or more equivalents of the appropriate acid or alkali in a solvent or medium in which the resulting salt is insoluble or in a solvent such as water which is removable by vacuum or by freeze-drying, or by exchanging the ions of an existing salt for another ion on a suitable ion exchange resin.

Carriers or excipients can also be used to facilitate the administration of a composition to a subject. Examples of carriers and excipients include, e.g., calcium carbonate, calcium phosphate, various sugars (e.g. lactose, glucose or sucrose), or various types of starch, cellulose derivatives, gelatin, vegetable oils (e.g. sesame oil, peanuts oil, olive oil), polyethylene glycols and physiologically compatible solvents. Compositions or pharmaceutical compositions can be administered by different routes including, e.g., intravenous, intraperitoneal, subcutaneous and intramuscular, oral, topical and transmucosal administration.

If desired, solutions of the compositions of the invention may be thickened with a thickening agent such as methylcellulose. They may be prepared in an emulsified form (e.g. water in oil or oil in water). Any of the pharmaceutically acceptable emulsifying agents known in the art may be employed including, e.g., acacia gum powder, a non-ionic surfactant (e.g. Tween), or an ionic surfactant (e.g. alkali polyether alcohol sulfates or sulfonates such as Triton).

Compositions may be sterilized by conventional sterilization techniques or filtering. Compositions may contain pharmaceutically acceptable auxiliary substances which have approximate physiological conditions as required, such as pH buffering agents. Useful buffers include, for example, sodium acetate/acetic acid buffers. A form of suppository or preparation with slow release function may be used so that pharmaceutically effective amounts of the preparation remain in the bloodstream over many hours or days following transdermal injection or delivery.

The desired isotonicity may be obtained by using sodium chloride or other pharmaceutically acceptable agents such as glucose, boric acid, sodium tartrate, propyleneglycol, polyols (e.g. mannitol and sorbitol), or other inorganic or organic solvents. Sodium chloride is preferred for buffers containing sodium ion.

In one embodiment, for a patient with a body weight of about 70 kg, the effective dosage of the compound will be in the range of about 0.01 or about 0.03 to about 5 mg per day, preferably about 0.01 or about 0.5 to about 2 mg per day, or more preferably about 0.01 or about 0.1 to about 1 mg per day, administered in one or more doses. The exact dose may be determined by the attending physician and is dependent upon whether the specific compound lies within the above quoted ranges, as well as upon the age, weight and symptom of the individual patient.

In certain embodiments, a PEG modified exendin or exendin analog as described herein may be administered to a subject to treat diabetes mellitus. In certain embodiments, administration of the compound should begin immediately at the time diabetes mellitus symptoms manifest or right after diabetes mellitus is diagnosed. Optionally, in other embodiments, the compound may be administered before symptoms manifest as a preventative treatment.

Although the compounds are typically used to treat human patients, they may be used to treat similar or identical diseases in other vertebrates as well, such as other primates, farm animals (e.g. swine, cattle and poultry), animals or pets for sports (e.g. horses, dogs and cats).

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

A linear PEG derivative with a molecular weight of 5,000 Da was purchased from Sigma-Aldrich Corporation. Other PEG derivatives used herein were purchased from Beijing JenKem Technology Co., Ltd.

A, B Double-Pump AKTA purifiers used in the ion exchange experiments, and other columns and packing were purchased from General Electric. Relevant reagents were purchased from Sigma-Aldrich. The native exendin-4 and its analogs used in Examples 3-9 were purchased from Chengdu Shennuo Science and Technology Co. Ltd.

Example 1

Solid Phase Synthesis of Exensin-4 Analogs

Example 1 presents a method of solid phase synthesis of the exendin-4 analog having the following amino acid sequences:

(SEQ ID NO: 232)
[His-Gly-Glu-Gly-Thr-Phe-Thr-Ser-Asp-Leu-Ser-Lys-

Gln-Arg-Glu-Glu-Glu-Ala-Val-Lys-Leu-Phe-Ile-Glu-

Trp-Leu-Lys-Asn-Gly-Gly-Pro-Ser-Ser-Gly-Ala-Pro-

Pro-Pro-Ser-OH].

(1) Amino Acid Residues:

| |
|---|
| Fmoc-L-Ala-OH |
| Fmoc-L-Asn(Trt)-OH |
| Fmoc-L-Asp(OtBu)-OH |
| Fmoc-L-Gln(Trt)-OH |
| Fmoc-L-Glu(OtBu)-OH |
| Fmoc-L-Gly-OH |
| Fmoc-L-His(Trt)-OH |
| Fmoc-L-Ile-OH |
| Fmoc-L-Leu-OH |
| Fmoc-L-Lys(Boc)-OH |
| Fmoc-L-Met-OH |
| Fmoc-L-Phe-OH |
| Fmoc-L-Pro-OH |
| Fmoc-L-Ser(tBu)-OH |
| Fmoc-L-Thr(tBu)-OH |
| Fmoc-L-Trp-OH |
| Fmoc-L-Tyr(tBu)-OH |
| Fmoc-L-Val-OH |

Wherein:
Fmoc refers to 9-Fluorenylmethoxycarbonyl;
BOC refers to tert-butyloxycarbonyl;
Trt refers to triphenylmethyl;
OtBu refers to tert-butyl ester;
tBu refers to tert-butyl.

(2) Apparatus and Reagents for the Synthesis

Peptide syntheses were conducted using a Peptide Synthesizer 433A (Applied Biosystem, USA).

Reagents used for these syntheses were N-Methylpyrrolidone, methylene dichloride, hexahydropyridine, methanol, dimethylaminopyridine/DMF, N,N-diisopropylethylamine/NMP, HBTU 100 mmole/0.5M HOBT in DMF, N,N-Dicyclohexylcarbodiimide/NMP.

Wherein:
DMF refers to N,N-Dimethylformamide,
NMP refers to N-Methylpyrrolidone,
HOBT refers to 1-Hydroxybenzotriazole,
HBTU refers to 2-1H-benzotriazole-yl-1,1,3,3-tetramethyl-Uroniumhexa-fluorophosphate.

(3) Procedures a. Synthesis

The quantities of the reagents used in the procedures below were based on a synthesis scale of 0.25 mmol. 0.25 g of HMP resin was weighed and placed in the synthesizer's reactor vessel. 1 mmol of various amino acids having protecting groups, were weighed and arrayed in the synthesizer in the order of the amino acid sequence of the desired insulinotropic peptide derivative from the C-terminus to the N-terminus. At a room temperature of 25° C., reactions for removing Fmoc protection, activating a residue and attaching the activated residue to HMP resin were automatically performed under the control of a computer program. Such reactions were repeated until the whole peptide was synthesized. After completion of the synthesis, the resin attached with the synthesized peptide having protecting groups to its amino acid side chains was air dried in the peptide synthesizer and then weighed.

b. Removal of Protecting Groups and Detachment of Resin

The resin attached with the synthesized peptide having protecting groups was placed in a plugged Ehrlenmeyer flask, and the cleavage reagent as shown below was added.

| Reagent | Amount |
| --- | --- |
| Water | 0.50 ml |
| Methyl-phenoxide | 0.50 ml |
| Phenol | 0.75 g |
| Mercaptoethanol | 0.20 ml |
| Trifluoroacetic acid (TFA) | 10.0 ml |

This reaction was carried out at constant temperature of 30° C. for six hours with constant stirring. After that, the mixture was filtered, the aqueous filtrates were collected, and the resin was rinsed with a small amount of Trifluoroacetic acid (TFA). The rinsing solution was mixed with the collected aqueous filtrates. Then the mixture was precipitated with ether and the precipitates were rinsed with a small amount of ether. The precipitates were dried in the drying apparatus to obtained the crude product.

c. Separation and Purification by HPLC and Lyophilization

The crude product was separated and purified by preparative HPLC, and then lyophilized to obtain the final product. The molecular weight of the product was analyzed using Chromatography and mass spectrometry. The theoretical molecular weight of the synthesized peptide was 4300.6 and the actual molecular weight measured was 4316.7.

Similarly, the above method can be used by a technician skilled in the art to synthesize other exendins or exendin analogs.

Example 2

Preparation of an Exendin-4 Analog by Genetic Engineering Techniques

This example describes a method to make the exendin-4 analog having the following amino acid sequences by a genetic engineering method:

(SEQ ID NO: 251)
[His-Gly-Glu-Gly-Thr-Phe-Thr-Ser-Asp-Leu-Ser-Lys-

Gln-Leu-Glu-Glu-Glu-Ala-Val-Lys-Leu-Phe-Ile-Glu-

Trp-Leu-Lys-Asn-Gly-Gly-Pro-Ser-Ser-Gly-Ala-Pro-

Pro-Pro-Ser-Arg-OH].

A. The following gene fragments were synthesized based on the amino acid sequences of the exendin analog to be produced:

(SEQ ID NO: 266)
(1) 5' AAT TCC ATG CAC GGC GAA ACC TTC ACC AGC GAT

CTG AGC AAA CAG CTG GAA GAA GAA GCG GTT AA (SEQ ID NO: 267)
(2) 5' ACTG TTC ATC GAA TGG CTG AAA AAC GGC GGC

CCG AGC AGC GGC CCG CCG CCG AGC CGT TAG A (SEQ ID NO: 268)
(3) 5' AGCTT CTA ACG GCT CGG CGG CGG CGC GCT GCT

CGG GCC GCC GTT TTT CAG CCA TTC GAT GA (SEQ ID NO: 269)
(4) 5' ACAG TTT AAC CGC TTC TTC TTC CAG CTG TTT

GCT CAG ATC GCT GGT GAA GGT GCC TTC GCC GTG CAT GG

B. Cloning

Ligation: Two test tubes were taken. Gene fragments (1) and (4) were added and mixed in one tube. Gene fragments (2) and (3) were added and mixed in the other tube. Polynucleotide kinase buffer, polynucleotide kinase, and adenosine triphosphates (ATP) were added to each tube. The reaction mixtures were incubated at 37° C. for 60 minutes to phosphorylated the 5' end of the gene fragments. The two tubes were placed in a 95° C. water bath to incubate for 10 minutes. Then the tubes were naturally cooled down to room temperature. T4 ligase buffer and T4 ligase were added to each tube, and the mixtures were incubated overnight at 16° C. to allow ligation of the gene fragments.

Plasmid: A plasmid containing a Lac promoter (a temperature control promoter PL, or a Tac promoter) was digested with restriction endonucleases EcoR I and Hind III and extracted with phenol/chloroform solution. The mixture was centrifuged and the aqueous phase was collected. The aqueous phase was extracted with chloroform and centrifuged for three times. The resulting aqueous phase was precipitated with isopropanol, centrifuged and air dried.

The digested plasmid and the ligated gene fragment were mixed together. T4 ligase buffer and T4 ligase were added to the mixture and incubated at room temperature for 3 to 4 hours.

Culturing of host cells: *E. coli* JM103 were incubated at 37° C. in LB culture solution containing 10 g of peptone, 5 g of yeast extract and 5 g of NaCl for 4 hours with shaking. The bacteria cultures were centrifuged and the precipitates were treated with $CaCl_2$ solution and kept at 4° C. for further use.

Transformation: The cloned plasmid was transformed into *E. coli* JM103 host cells. The transformed bacteria cells were incubated in an ice bath for 30 minutes, and then incubated at 42° C. for 2 minutes. The bacteria cells were spread out on an agar plate containing Ampicillin and were incubated overnight at 37° C. Colonies grown on the agar plate were selected as the positive clones containing the recombinant plasmids.

C. Fermentation

The selected host bacteria strain containing the desired plasmid was incubated with shaking in LB culture solution. 0.5 mM of Isopropyl beta-D-thiogalactopyranoside (IPTG) was added to the culture solution to induce expression of the desired peptide. After overnight incubation, the bacteria cells were harvested by centrifugation. The expressed peptides were identified by polyacrylamide gel electrophoresis (PAGE) containing 12% SDS.

D. Inclusion Bodies

Ten bottles, each containing 300 ml of bacteria cultures, were incubated with shaking under the conditions described above. After induction of protein expression, lysis solution (20 mM of phosphoric acid buffer containing 1% NaCl, pH 7.5) and lysozyme were added to the culture solution and incubated at 30° C. for 30 minutes and then centrifuged to collect the precipitates. The collected precipitates were treated with 6M guanidine hydrochloride (Gu.HCl) to dissolve the inclusion bodies. The solution was centrifuged, and the resulting supernatant was dialyzed to remove the Gu.HCl. The precipitates resulting from the dialysis were rinsed three times with 20 mM phosphoric acid buffer (pH 7.5) containing 1% NaCl and 0.1% Tween 80 to obtain the inclusion bodies.

E. Degradation

The inclusion bodies were dissolved in 8 M urea solution. Then hydrochloric acid and cyanogen bromide were added to the solution. The final concentration of hydrochloric acid in the solution was 50 mM. The solution was stirred in dark and under nitrogen gas protection for 2 hours to break up the inclusion bodies. HPLC analysis was used to monitor the process.

F. Purification

After the inclusion bodies were broken up, the crude product was obtained through Sepharose G-25 chromatography. The crude product was further purified by HPLC to obtain the final product. Similar to the product synthesized through chemical process, the experimental molecular weight of the obtained peptide measured by mass spectrometry was consistent with its theoretical molecular weight.

Example 3

Exendin-4 Modified with Linear Methoxy-Polyethylene Glycol (mPEG) Derivatives (Mf: 5,000 Da)

1.0 mg of exendin-4 was put into each of three tubes, and dissolved in phosphoric acid buffer having different pH values, respectively. 5.8 mg of N-Hydroxysuccinimide-activated mPEG (Mf: 5,000 Da) was added to each tube. The mixtures were placed on a shaking table for an hour at room temperature. The resulting products were analyzed to measure the amount of the un-modified exendin-4 using Agilent 1100 HPLC (Analysis conditions are: 0.1% phosphoric acid as solvent A and 0.1% phosphoric acid+80% acetonitrile as Solvent B, gradient: 35%-70% solvent B/25 minutes). The results are as follows:

Effects of Different pH Values on Exendin-4 Pegylation

| pH values | Un-modified Exendin-4 |
|---|---|
| 6.5 | 52% |
| 7.5 | 21% |
| 8.5 | 4% |

A solution (pH value 3-4) containing mPEG modified exendin-4 was obtained after acetonitrile was removed from the solution obtained by reverse phase separation above.

Example 4

Exendin-4 Analogs Modified with Linear mPEG Derivatives (Mn: 21,000 Da)

1.0 mg exendin-4 analog was mixed with 2.0 ml of phosphoric acid buffer (pH 4.5) containing $NaBH_3CN$. 5.0 mg of aldehyde activated mPEG derivatives with a molecular weight of 21,000 Da was mixed with the exendin-4 analog and placed on the shaking table reacting overnight at room temperature. The reaction solution was purified by Agilent 1100 Chromatography using Zorbax SB-300 Semi-Preparative Column (Analysis conditions are: 0.1% phosphoric acid as solvent A and 0.1% phosphoric acid+80% acetonitrile as Solvent B, gradient: 35%-70% solvent B/25 minutes). An exendin-4 analog modified by mPEG at the N-terminus was thereafter obtained.

After the acetonitrile was removed from the solution collected above with a rotary evaporator, a desalting column was used to exchange the buffer of the modified exendin-4, which was then dissolved in the phosphoric acid buffer (pH 7.0-8.0) with 0.001-1.0% (w/v).3-methylphenol.

Example 5

Exendin-4 Analog Modified with mPEG Derivatives (Mn: 40,000 Da) Having the Structure of Formula IV 1.0 mg of an exendin-4 analog (SEQ ID NO: 251) was added into 4.0 ml phosphoric acid buffer (pH 7.0). 280 mg of N-Hydroxysuccinimide-activated mPEG derivative (Formula IV) with a molecular weight of 40,000 Da was mixed with the exendin-4 analog prepared above, and placed on the shaking table reacting for an hour at room temperature. After that, the reaction mixture was diluted with 200 ml Bristris buffer (pH 7.0) in a 250 ml beaker for further use.

Figure 3:
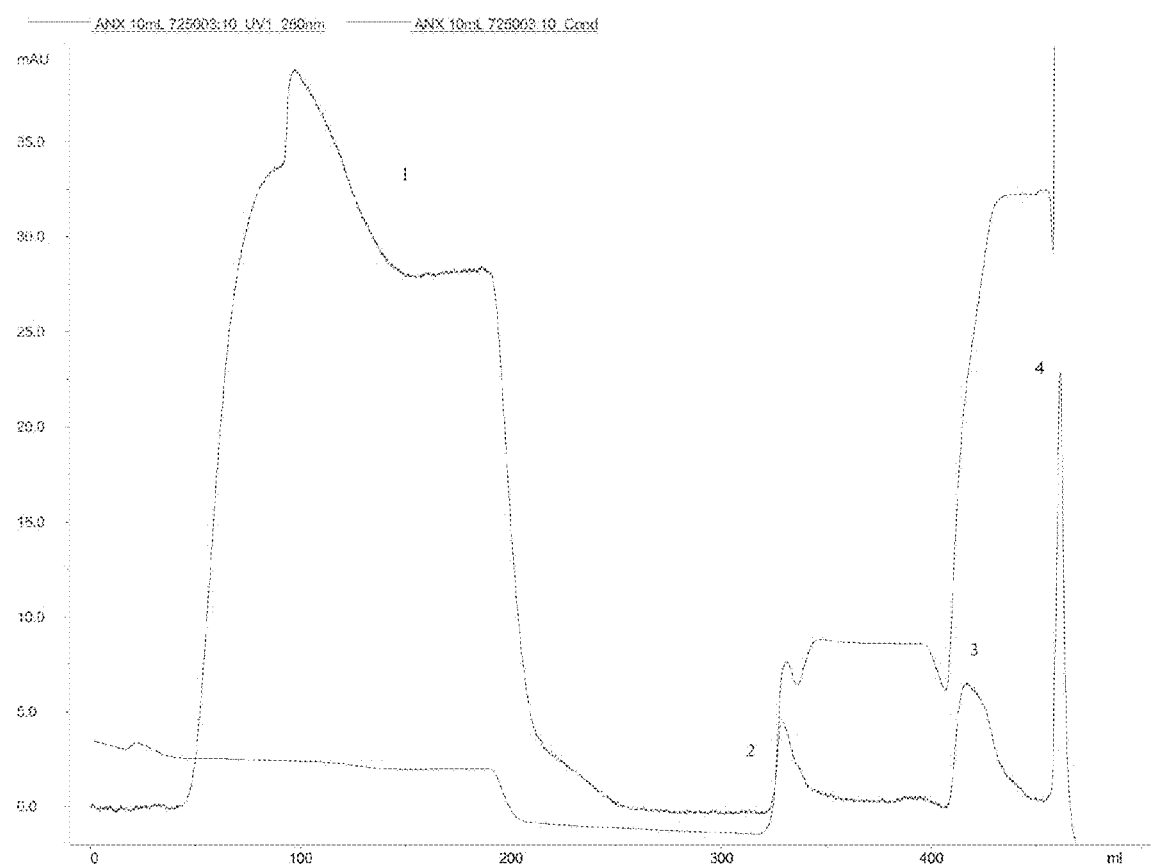
FIG. 3 shows the chromatography results from the separation and purification of an exendin-4 analog modified by PEG derivative (Formula IV) having a molecular weight of 40,000 Da (Dalton). Label 1 indicates the absorption peak at the time of sample loading; Label 2 indicates the absorption peak at the time of elution, showing exendin-4 analogs modified by multiple PEG derivatives; Label 3 indicates the absorption peak at the time of elution, showing exendin-4 analogs modified by single PEG derivatives, and Label 4 indicates the absorption peak at the time of elution, showing unmodified exendin-4 analog.
Figure 4:
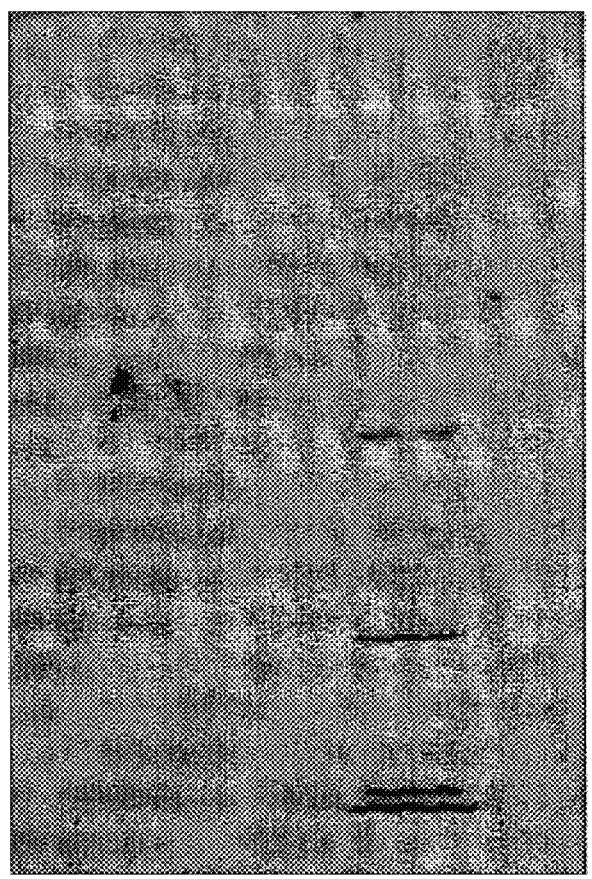
FIG. 4 is the electrophoretogram of an exendin-4 analog modified by a single PEG derivative (Formula IV) having a molecular weight of 40,000 Da, wherein lane 1 shows the band of the exendin-4 analog modified by a single PEG derivative.

A DEAE FF or ANX FF anion exchange column was equilibrated with Bistris buffers (pH 7.0). The diluted reaction mixture was loaded to the anion exchange column to allow the target substance to absorb onto the anion exchange resin. Single or multiple modified exendin-4 analogs were eluted through linear gradient elution of NaCl at different concentrations, and the eluent was collected with a fraction collector. The un-modified exendin-4 peptide was then eluted by using 1M NaCl. The eluent fractions from the separation and purification process was shown in FIG. 3, wherein labels 2, 3 and 4 indicated the elution peaks of multiple mPEG modified exendin-4 analog, single mPEG modified exendin-4 analog and un-modified exendin-4 analog, respectively. The modified exendin-4 analog was run by gel electrophoresis with SDS-PAGE. The molecular weight of the modified exendin-4 analog (with theoretical molecular weight of 44,300 Da) determined by SDS-PAGE was slightly higher than 43,000 Da (FIG. 4), indicating that the product obtained was really the single mPEG derivatives (Mn: 40,000 Da) modified exendin-4 analog.

The collected eluent containing single mPEG modified exendin-4 analog was concentrated using ultrafiltration equipment (an ultrafiltration centrifuge tube or an ultrafiltration device). The concentrated solution was loaded onto a desalting column to exchange into acetic acid buffer. Finally, isotonic adjustment agent (such as mannitol and 0.9% NaCl) and 0.001-1.0% (w/v) antibacterial reagent (such as 3-methylphenol) were added into the acetic acid buffer containing the modified exendin-4 analog.

Example 6

24-Hour Drug Effect Test of Single mPEG Derivatives (Mf: 5,000 Da and Mn: 21,000 Da) Modified Exendin Analogs Test Animal: C57 mice, 20 g+/−2 g, 8 mice for each group, a total of 4 groups.

Control Group 1: Sterile water was injected subcutaneously to each mouse.

Control Group 2: 0.025 μg exendin-4 analog was injected subcutaneously to each mouse.

Drug Group 1: 0.625 μg of exendin-4 analog modified by single mPEG derivatives (Mf: 5,000 Da) was injected subcutaneously to each mouse.

Drug Group 2: 0.625 μg of exendin-4 analog modified by single mPEG derivatives (Mn: 21,000 Da) was injected subcutaneously to each mouse.

Figure 5:
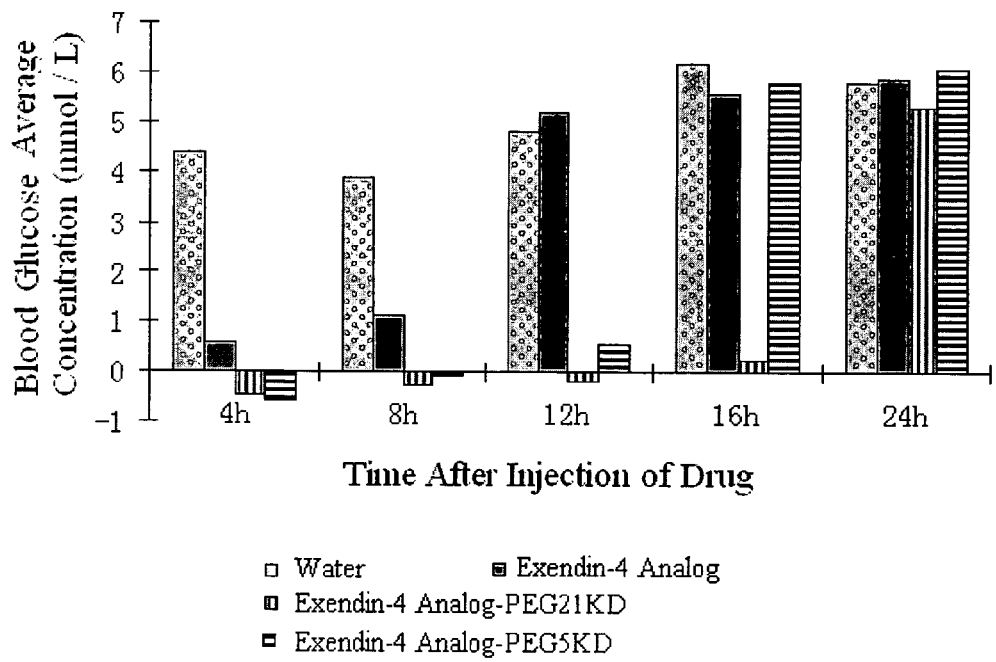
FIG. 5 shows the results of 24-hour drug effect test of exendin-4 analogs modified by a single PEG derivative having molecular weights of 5,000 and 21,000 Da, respectively, on animals.

Blood sample was taken from each mice group at 4, 8, 12, 16 and 24 hours after drug injection. 200 μl of 20% glucose solution was injected into the abdomen of each mouse 30 minutes before the blood sampling. The blood sugar level was measured using a glucose reagent kit (Shanghai ShenSuo Reagents Co., Ltd.). As shown in FIG. 5, the exendin-4 analogs modified with mPEG derivatives (Mn: 21,000 Da) remained effective 16 hours after injection. The effective period for exendin-4 analog modified with mPEG (Mf: 5,000 Da) was between 12 to 16 hours after drug injection. The effective period for un-modified exendin-4 analogs was less than 12 hours. The effective period for lowering the blood sugar level was longer using exendin-4 analogs modified by linear mPEG derivatives with a larger molecular weight than exendin-4 analogs modified by linear mPEG derivatives with a smaller molecular weight.

Example 7

72-Hour Drug Effect Test of Exendin Analogs Modified with Linear mPEG (Mn=21,000 Da) and Branched mPEG Having the Structure of Formula IV (Mn=40,000 Da)

Test Animal: C57 mice, 20 g+/−2 g, 8 mice for each group, a total of 5 groups.

Control Group 1: Sterile water was injected subcutaneously to each mouse.

Control Group 2: 0.025 µg of exendin-4 peptide was injected subcutaneously to each mouse.

Control Group 3: 0.025 µg of exendin analog was injected subcutaneously to each mouse.

Drug Group 1: 0.625 µg of exendin-4 analog modified by mPEG (Mn: 21,000 Da) was injected subcutaneously to each mouse.

Drug Group 2: 0.625 µg of exendin-4 analog modified by mPEG (Mn: 40,000 Da) was injected subcutaneously to each mouse.

Figure 6:
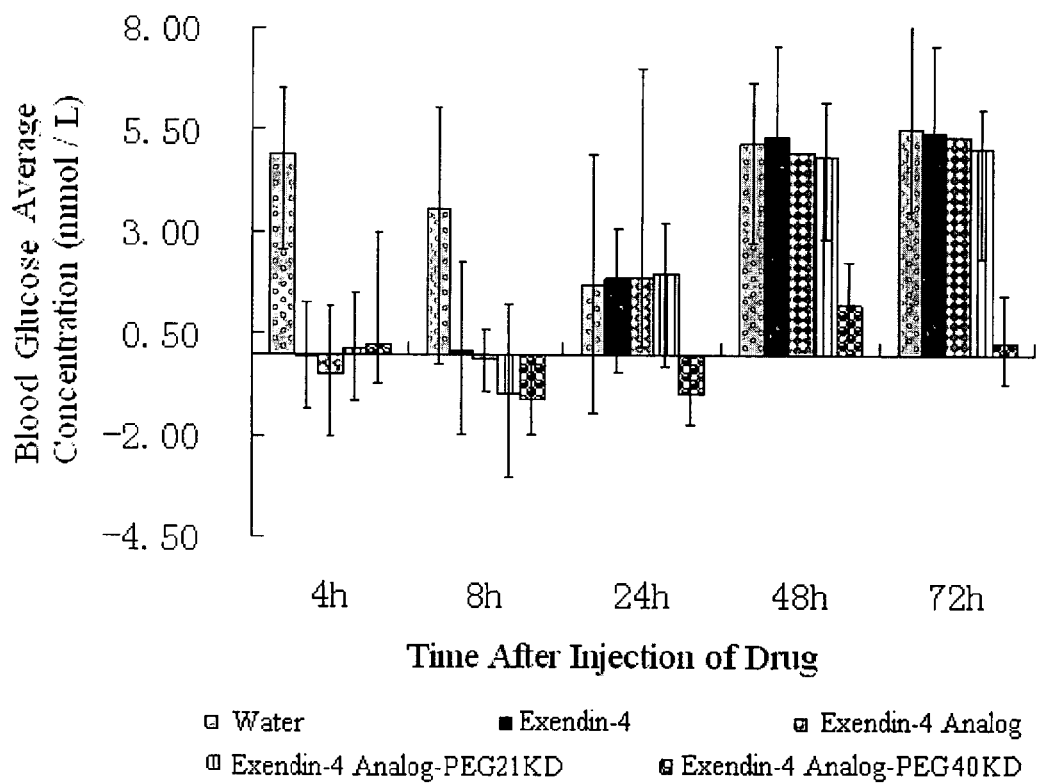
FIG. 6 shows the results of 72-hour drug effect test of exendin-4 analogs modified by a single linear or branched (Formula IV) PEG derivative having molecular weights of 21,000 and 40,000 Da on animals.

Blood samples were taken from each mice group at 4, 8, 24, 48 and 72 hours after drug injection. 200 µl of 20% glucose solution was injected into the abdomen of each mouse 30 minutes before each blood sampling. The blood sugar level was measured using the glucose reagent kit. As shown in FIG. 6, the exendin-4 analog modified by a branched PEG derivatives (Mn: 40,000 Da) remained effective for at least 72 hours after drug injection. The exendin-4 analog modified by linear mPEG derivatives (Mn: 21,000 Da) remained effective for about 24 hours after drug injection.

Example 8

Drug Effect Test of Exendin-4 Analogs Modified by Single mPEG Derivatives

Test Samples: a total of 8 samples, exendin-4 analogs modified by single mPEG derivatives (Formula II) with molecular weights of 21,000 Da, 30,000 Da, 40,000 Da, respectively; exendin-4 analogs modified by single mPEG derivatives (Formula IV) with molecular weights of 21,000 Da, 30,000 Da, 40,000 Da, respectively; exendin-4 analogs modified by linear mPEG derivatives with molecular weights of 21,000 Da and 30,000 Da, respectively.

Test Animal: C57 mice, 20 g+/−2 g, 3 sampling groups, 24 mice for each sampling group.

Because the mice could not endure frequent blood sampling, we designed to take blood from the sampling groups at different time after injecting the samples. The blood sampling schedule after drug injection was listed as follows:

| The First Group | The Second Group | The Third Group |
|---|---|---|
| 2, 8, 72 Hour | 4, 24, 48 Hour | 16, 36, 60 Hour |

Figure 7:
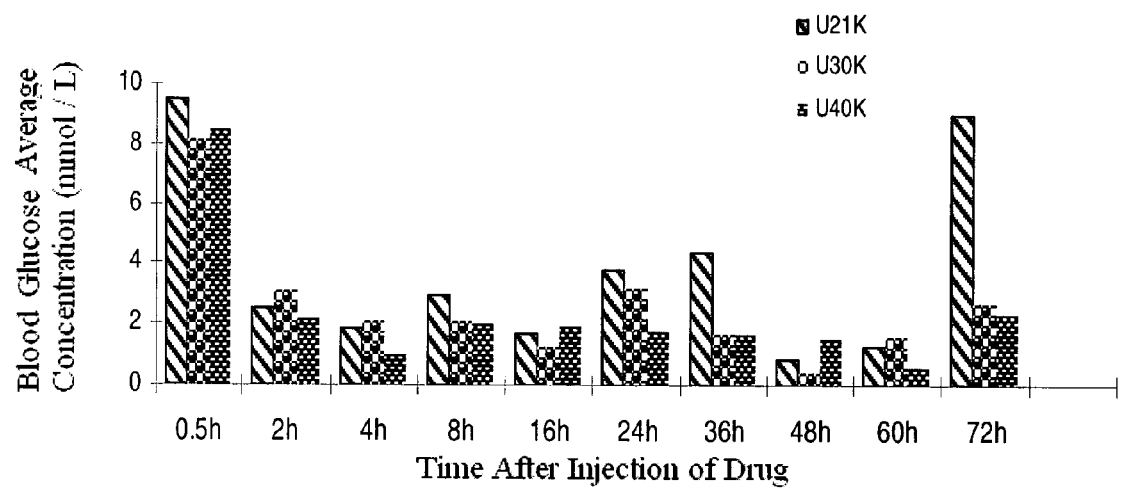
FIG. 7 shows the results of 72-hour drug effect test of exendin-4 analogs modified by single PEG derivatives (Formula II) having molecular weights of 21,000 Da (U21K), 30,000 Da (U30K) and 40,000 Da (U40K), respectively, on animals.
Figure 8:
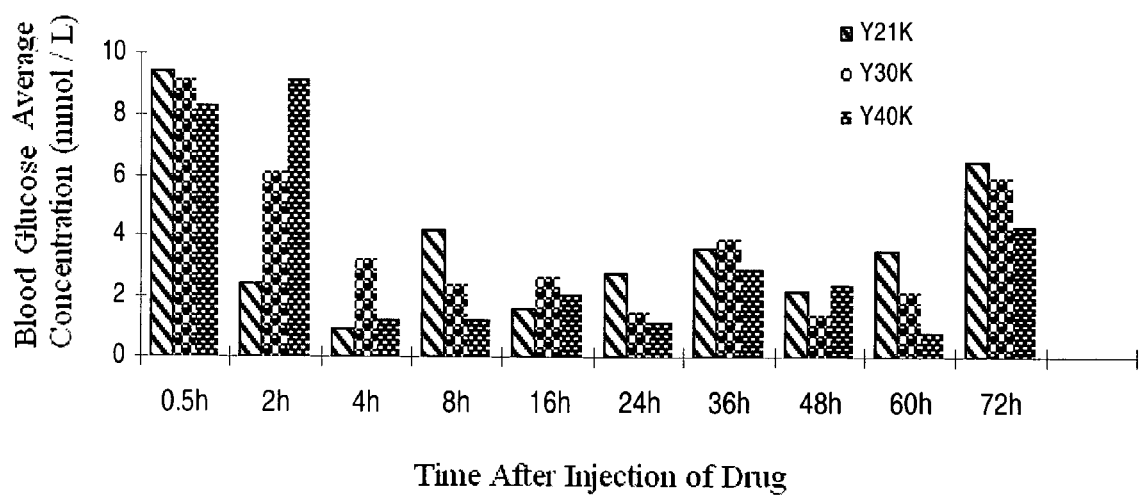
FIG. 8 shows the results of 72-hour drug effect test of exendin-4 analogs modified by single PEG derivatives (Formula IV) having molecular weights of 21,000 Da (Y21K), 30,000 Da (Y30K) and 40,000 Da (Y40K), respectively, on animals.
Figure 9:
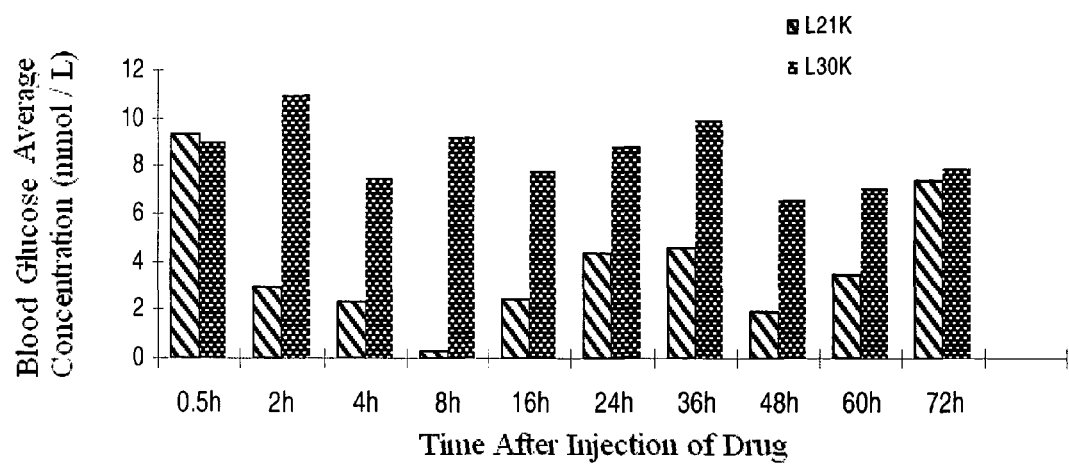
FIG. 9 shows the results of 72-hour drug effect test of exendin-4 analogs modified by single linear PEG derivatives having molecular weights of 21,000 Da (L21K) and 30,000 Da (L30k), respectively, on animals.

Each sampling group was further divided into 8 sub-groups. Every sub-group consisted of 3 mice. At the beginning of the test, each sub-group was injected with a different modified exendin-4 analog, which was referred to as L21K, L30K (modification by single linear mPEG derivatives having molecular weights of 21,000 Da and 30,000 Da, respectively); Y21K, Y30K, Y40K (modification by single mPEG derivatives having the structure of Formula IV and molecular weights of 21,000 Da, 30,000 Da and 40,000 Da, respectively), U21K, U30K, U40K (exendin-4 analogs modified with a single mPEG having the structure of Formula II and molecular weights of 21,000 Da, 30,000 Da and 40,000 Da, respectively). All of the different mPEG modified Exendin-4 analogs contained 0.625 µg of Exendin-4 analogs. 200 µl 20% glucose was injected into the abdominal space of the mice right after the drug injection. After half an hour, blood samples were taken from all mice. Subsequent blood sampling was conducted according to the sampling schedule table above. 200 µl 20% glucose was injected into the abdominal space of the mice half an hour prior to each blood sampling. FIGS. 7-9 showed that the molecular structure and weight of the PEG derivatives had great influence on the bioactivity of the exendin-4 analogs. The bioactivity of exendin-4 analogs modified by single mPEG having the structure of Formula II remains effective for a longer time than the exendin-4 analogs modified by PEG having the structure of Formula IV and the linear PEG in the 72 hours after drug injection. For the exendin-4 analogs modified by single PEG having the same branched structure, the greater molecular weight they had, the better bioactivity of lowering the blood sugar level they exhibited during the 72 hours. L30K has no noticeable bioactivity by the 72 hours after drug injection, which showed that higher molecular weight of linear PEG had a negative effect on the modified Exendin-4 analog's bioactivity.

Example 9

Pharmacokinetics Test of Exendin-4 Analogs Modified by Single PEG

Test Animal: SD mice, male, 250 g-300 g, 2 groups, 4 mice for each group.

Drug Group 1: The mice were each injected with exendin-4 analogs (SEQ ID NO: 251) modified by single mPEG derivatives (Formula II, Mn: 30,000 Da) containing 4.375 µg Exendin-4 analogs (U30K).

Drug Group 2: The mice were each injected with exendin-4 analog (SEQ ID NO: 251) modified by single mPEG derivatives (Formula IV, Mn: 40,000 Da) containing 4.375 µg Exendin-4 analogs (Y40K).

Figure 10:
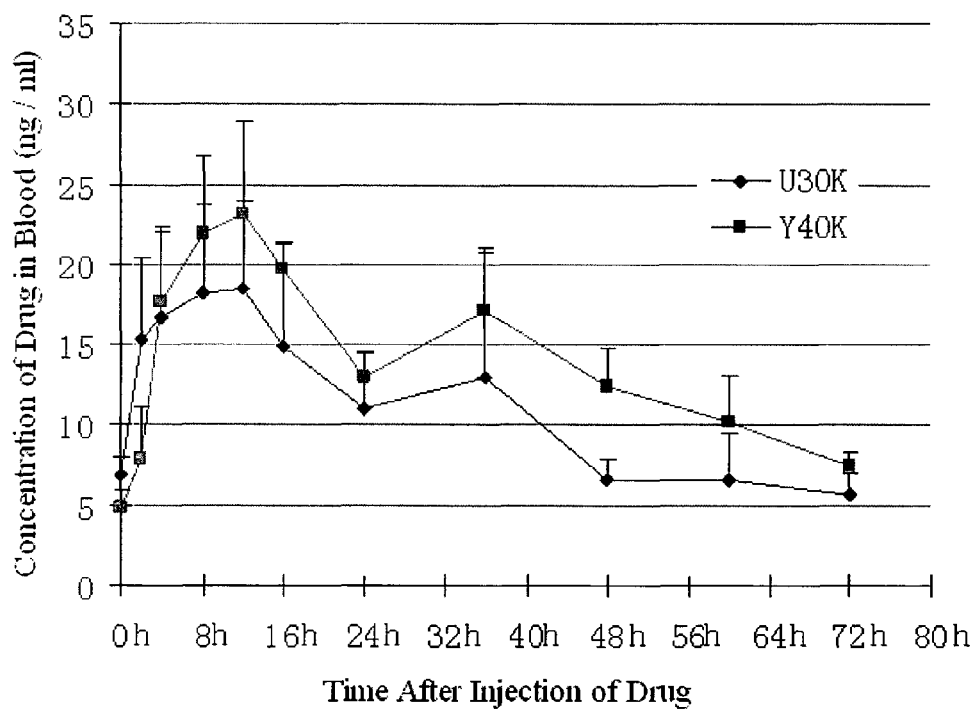
FIG. 10 shows the results of 72-hour drug pharmacokinetics test of exendin-4 analogs modified by single PEG derivatives (Formula II) having molecular weights of 30,000 Da (U30K) and PEG derivatives (Formula IV) having molecular weights of 40,000 Da (Y40K), respectively.

Blood samples were taken from every mice group at 0, 2, 4, 8, 12, 16, 24, 36, 48, 60 and 72 hours after the drug injection. The concentration of exendin-4 in the blood was tested using Enzyme Immunoassay kit (EIA) purchased from Phoenix Pharmaceuticals, Inc., California, U.S.A. The data was analyzed by Pharmaceutical Kinetics Software 1.0.2 (Shanghai Hongneng Software Co. Ltd.), and the results were shown in FIG. 10. The time taken for half of the U30K to be absorbed was 10.78 hours and the time taken for half of the U30K to be eliminated was 21.44 hours. The time taken for half of the Y40K to be absorbed was 5.53 hours and the time taken for half of the Y40K to be eliminated was 40.77 hours. The time for the two samples to reach peak concentration in the blood was about 12 hours after injecting the drug. The peak concentration of the two samples in the blood was about 20 ng/ml.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein.

The invention claimed is:

1. A PEG modified exendin or exendin analog comprising one or more PEG derivatives linked to one or more amino acids of said exendin or exendin analog, wherein the molecular weight of said one or more PEG derivatives exceeds 20,000 Da, and said one or more PEG derivatives comprise a branched structure set forth in Formula IV below:

$$\begin{array}{c} \text{MePEG} \\ \diagdown \\ \text{N}-\text{CH}_2- \\ \diagup \\ \text{MePEG}-\text{C} \\ \parallel \\ \text{O} \end{array} \quad (IV)$$

wherein PEG is —O(CH$_2$CH$_2$O)$_q$, q is a positive integer, and Me is a methyl group.

2. The PEG modified exendin or exendin analog of claim 1, wherein the exendin or exendin analog comprises the amino acid sequence set forth in SEQ ID NO: 1.

3. The PEG modified exendin or exendin analog of claim 1, wherein the exendin or exendin analog comprises the amino acid sequence set forth in SEQ ID NO: 2.

4. The PEG modified exendin or exendin analog of claim 1, wherein the exendin or exendin analog comprises one or more amino acid sequences set forth in SEQ ID NO: 3 to NO: 229.

5. The PEG modified exendin or exendin analog of claim 1, wherein the exendin or exendin analog comprises one or more amino acid sequences set forth in SEQ ID NO: 230 to NO: 265.

6. The PEG modified exendin or exendin analog of claim 1, wherein said one or more PEG derivatives have a molecular weight in the range of above 20,000 Da to about 50,000 Da.

7. The PEG modified exendin or exendin analog of claim 1, wherein said one or more PEG derivatives are activated to link to said exendin or exendin analog by N-Hydroxysuccinimide.

8. The PEG modified exendin or exendin analog of claim 1 comprising one, two, three or four branched PEG derivatives.

9. The PEG modified exendin or exendin analog of claim 8 comprising one branched PEG derivative.

10. A composition comprising a PEG modified exendin or exendin analog of claim 1.

11. A method of treating diabetes mellitus comprising administering a PEG modified exendin or exendin analog of claim 1 to a subject.

* * * * *

```
                           SEQUENCE LISTING

<160> NUMBER OF SEQ ID NOS: 269

<210> SEQ ID NO 1
<211> LENGTH: 39
<212> TYPE: PRT
<213> ORGANISM: Heloderma horridum

<400> SEQUENCE: 1

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma horridum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30
<212> TYPE: PRT
<213> ORGANISM: Artificial Sequence
<220> FEATURE:
<223> OTHER INFORMATION: Exendin Analog 1

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Exendin Analog 2

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30
```

```
<210> SEQ ID NO 5
<211> LENGTH: 28
<212> TYPE: PRT
<213> ORGANISM: Artificial Sequence
<220> FEATURE:
<223> OTHER INFORMATION: Exendin Analog 3

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 6
<211> LENGTH: 39
<212> TYPE: PRT
<213> ORGANISM: Artificial Sequence
<220> FEATURE:
<223> OTHER INFORMATION: Exendin Analog 4

<400> SEQUENCE: 6

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 7
<211> LENGTH: 28
<212> TYPE: PRT
<213> ORGANISM: Artificial Sequence
<220> FEATURE:
<223> OTHER INFORMATION: Exendin Analog 5

<400> SEQUENCE: 7

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Exendin Analog 6

<400> SEQUENCE: 8

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 9
<211> LENGTH: 18
<212> TYPE: PRT
<213> ORGANISM: Artificial Sequence
<220> FEATURE:
<223> OTHER INFORMATION: Exendin Analog 7
<220> FEATURE:
<221> NAME/KEY: MOD_RES
<222> LOCATION: (9)..(9)
<223> OTHER INFORMATION: pentylglycine

<400> SEQUENCE: 9
```

His Gly Glu Phe Thr Ser Asp Leu Xaa Phe Ile Glu Phe Pro Pro Pro
1               5                   10                  15

Pro Ser

<210> SEQ ID NO 10
<211> LENGTH: 18
<212> TYPE: PRT
<213> ORGANISM: Artificial Sequence
<220> FEATURE:
<223> OTHER INFORMATION: Exendin Analog 8
<220> FEATURE:
<221> NAME/KEY: MOD_RES
<222> LOCATION: (10)..(10)
<223> OTHER INFORMATION: naphthylalanine

<400> SEQUENCE: 10

His Gly Glu Phe Thr Ser Asp Leu Met Xaa Ile Glu Trp Pro Pro Pro
1               5                   10                  15

Pro Ser

<210> SEQ ID NO 11
<211> LENGTH: 20
<212> TYPE: PRT
<213> ORGANISM: Artificial Sequence
<220> FEATURE:
<223> OTHER INFORMATION: Exendin Analog 9

<400> SEQUENCE: 11

His Gly Glu Phe Thr Ser Asp Leu Met Phe Val Ala Leu Glu Trp Pro
1               5                   10                  15

Pro Pro Pro Ser
         20

<210> SEQ ID NO 12
<211> LENGTH: 20
<212> TYPE: PRT
<213> ORGANISM: Artificial Sequence
<220> FEATURE:
<223> OTHER INFORMATION: Exendin Analog 10

<400> SEQUENCE: 12

His Gly Glu Phe Thr Ser Asp Leu Leu Phe Val Ala Leu Glu Phe Pro
1               5                   10                  15

Pro Pro Pro Ser
         20

<210> SEQ ID NO 13
<211> LENGTH: 18
<212> TYPE: PRT
<213> ORGANISM: Artificial Sequence
<220> FEATURE:
<223> OTHER INFORMATION: Exendin Analog 11
<220> FEATURE:
<221> NAME/KEY: MOD_RES
<222> LOCATION: (11)..(11)
<223> OTHER INFORMATION: tert-butylglycine

<400> SEQUENCE: 13

His Gly Glu Phe Thr Ser Asp Leu Met Phe Xaa Glu Trp Pro Pro Pro
1               5                   10                  15

Pro Ser

<210> SEQ ID NO 14
<211> LENGTH: 18

<212> TYPE: PRT
<213> ORGANISM: Artificial Sequence
<220> FEATURE:
<223> OTHER INFORMATION: Exendin Analog 12
<220> FEATURE:
<221> NAME/KEY: MOD_RES
<222> LOCATION: (11)..(11)
<223> OTHER INFORMATION: tert-butylglycine

<400> SEQUENCE: 14

His Gly Glu Phe Thr Ser Asp Leu Leu Phe Xaa Glu Phe Pro Pro Pro
1               5                   10                  15

Pro Ser

<210> SEQ ID NO 15
<211> LENGTH: 18
<212> TYPE: PRT
<213> ORGANISM: Artificial Sequence
<220> FEATURE:
<223> OTHER INFORMATION: Exendin Analog 13

<400> SEQUENCE: 15

His Gly Glu Phe Thr Ser Asp Leu Met Phe Ile Asp Trp Pro Pro Pro
1               5                   10                  15

Pro Ser

<210> SEQ ID NO 16
<211> LENGTH: 18
<212> TYPE: PRT
<213> ORGANISM: Artificial Sequence
<220> FEATURE:
<223> OTHER INFORMATION: Exendin Analog 14

<400> SEQUENCE: 16

His Ala Glu Phe Thr Ser Asp Leu Leu Phe Ile Glu Phe Pro Pro Pro
1               5                   10                  15

Pro Ser

<210> SEQ ID NO 17
<211> LENGTH: 18
<212> TYPE: PRT
<213> ORGANISM: Artificial Sequence
<220> FEATURE:
<223> OTHER INFORMATION: Exendin Analog 15
<220> FEATURE:
<221> NAME/KEY: MOD_RES
<222> LOCATION: (14)..(17)
<223> OTHER INFORMATION: homoproline

<400> SEQUENCE: 17

His Gly Glu Phe Thr Ser Asp Leu Met Phe Ile Glu Trp Xaa Xaa Xaa
1               5                   10                  15

Xaa Ser

<210> SEQ ID NO 18
<211> LENGTH: 18
<212> TYPE: PRT
<213> ORGANISM: Artificial Sequence
<220> FEATURE:
<223> OTHER INFORMATION: Exendin Analog 16
<220> FEATURE:
<221> NAME/KEY: MOD_RES
<222> LOCATION: (15)..(17)
<223> OTHER INFORMATION: homoproline

<400> SEQUENCE: 18

-continued

```
His Gly Glu Phe Thr Ser Asp Leu Met Phe Ile Glu Trp Pro Xaa Xaa
1               5                   10                  15

Xaa Ser

<210> SEQ ID NO 19
<211> LENGTH: 17
<212> TYPE: PRT
<213> ORGANISM: Artificial Sequence
<220> FEATURE:
<223> OTHER INFORMATION: Exendin Analog 17
<220> FEATURE:
<221> NAME/KEY: MOD_RES
<222> LOCATION: (14)..(16)
<223> OTHER INFORMATION: homoproline

<400> SEQUENCE: 19

His Gly Glu Phe Thr Ser Asp Leu Met Phe Ile Glu Trp Xaa Xaa Xaa
1               5                   10                  15

Ser

<210> SEQ ID NO 20
<211> LENGTH: 18
<212> TYPE: PRT
<213> ORGANISM: Artificial Sequence
<220> FEATURE:
<223> OTHER INFORMATION: Exendin Analog 18
<220> FEATURE:
<221> NAME/KEY: MOD_RES
<222> LOCATION: (15)..(17)
<223> OTHER INFORMATION: homoproline

<400> SEQUENCE: 20

His Gly Glu Phe Thr Ser Asp Leu Met Phe Ile Glu Trp Pro Xaa Xaa
1               5                   10                  15

Xaa Ser

<210> SEQ ID NO 21
<211> LENGTH: 18
<212> TYPE: PRT
<213> ORGANISM: Artificial Sequence
<220> FEATURE:
<223> OTHER INFORMATION: Exendin Analog 19
<220> FEATURE:
<221> NAME/KEY: MOD_RES
<222> LOCATION: (14)..(17)
<223> OTHER INFORMATION: homoproline

<400> SEQUENCE: 21

His Gly Glu Phe Thr Ser Asp Leu Leu Phe Ile Glu Phe Xaa Xaa Xaa
1               5                   10                  15

Xaa Ser

<210> SEQ ID NO 22
<211> LENGTH: 18
<212> TYPE: PRT
<213> ORGANISM: Artificial Sequence
<220> FEATURE:
<223> OTHER INFORMATION: Exendin Analog 20
<220> FEATURE:
<221> NAME/KEY: MOD_RES
<222> LOCATION: (14)..(17)
<223> OTHER INFORMATION: homoproline

<400> SEQUENCE: 22

His Gly Glu Phe Thr Ser Asp Leu Leu Phe Ile Glu Phe Xaa Xaa Xaa
1               5                   10                  15
```

```
Xaa Ser

<210> SEQ ID NO 23
<211> LENGTH: 18
<212> TYPE: PRT
<213> ORGANISM: Artificial Sequence
<220> FEATURE:
<223> OTHER INFORMATION: Exendin Analog 21
<220> FEATURE:
<221> NAME/KEY: MOD_RES
<222> LOCATION: (14)..(17)
<223> OTHER INFORMATION: N-methylalanine

<400> SEQUENCE: 23

His Gly Glu Phe Thr Ser Asp Leu Met Phe Ile Glu Trp Xaa Xaa Xaa
1               5                   10                  15

Xaa Ser

<210> SEQ ID NO 24
<211> LENGTH: 18
<212> TYPE: PRT
<213> ORGANISM: Artificial Sequence
<220> FEATURE:
<223> OTHER INFORMATION: Exendin Analog 22
<220> FEATURE:
<221> NAME/KEY: MOD_RES
<222> LOCATION: (15)..(17)
<223> OTHER INFORMATION: N-methylalanine

<400> SEQUENCE: 24

His Gly Glu Phe Thr Ser Asp Leu Met Phe Ile Glu Trp Pro Xaa Xaa
1               5                   10                  15

Xaa Ser

<210> SEQ ID NO 25
<211> LENGTH: 18
<212> TYPE: PRT
<213> ORGANISM: Artificial Sequence
<220> FEATURE:
<223> OTHER INFORMATION: Exendin Analog 23
<220> FEATURE:
<221> NAME/KEY: MOD_RES
<222> LOCATION: (14)..(17)
<223> OTHER INFORMATION: N-methylalanine

<400> SEQUENCE: 25

His Gly Glu Phe Thr Ser Asp Leu Leu Phe Ile Glu Phe Xaa Xaa Xaa
1               5                   10                  15

Xaa Ser

<210> SEQ ID NO 26
<211> LENGTH: 30
<212> TYPE: PRT
<213> ORGANISM: Artificial Sequence
<220> FEATURE:
<223> OTHER INFORMATION: Exendin Analog 24

<400> SEQUENCE: 26

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 27
<211> LENGTH: 28
<212> TYPE: PRT
```

```
<213> ORGANISM: Artificial Sequence
<220> FEATURE:
<223> OTHER INFORMATION: Exendin Analog 25

<400> SEQUENCE: 27

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 28
<211> LENGTH: 28
<212> TYPE: PRT
<213> ORGANISM: Artificial Sequence
<220> FEATURE:
<223> OTHER INFORMATION: Exendin Analog 26

<400> SEQUENCE: 28

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: Exendin Analog 27

<400> SEQUENCE: 29

His Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: Exendin Analog 28

<400> SEQUENCE: 30

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 31
<211> LENGTH: 28
<212> TYPE: PRT
<213> ORGANISM: Artificial Sequence
<220> FEATURE:
<223> OTHER INFORMATION: Exendin Analog 29

<400> SEQUENCE: 31

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 32
<211> LENGTH: 28
```

```
<212> TYPE: PRT
<213> ORGANISM: Artificial Sequence
<220> FEATURE:
<223> OTHER INFORMATION: Exendin Analog 30

<400> SEQUENCE: 32

His Gly Glu Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 33
<211> LENGTH: 28
<212> TYPE: PRT
<213> ORGANISM: Artificial Sequence
<220> FEATURE:
<223> OTHER INFORMATION: Exendin Analog 31

<400> SEQUENCE: 33

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 34
<211> LENGTH: 28
<212> TYPE: PRT
<213> ORGANISM: Artificial Sequence
<220> FEATURE:
<223> OTHER INFORMATION: Exendin Analog 32

<400> SEQUENCE: 34

His Gly Glu Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 35
<211> LENGTH: 28
<212> TYPE: PRT
<213> ORGANISM: Artificial Sequence
<220> FEATURE:
<223> OTHER INFORMATION: Exendin Analog 33

<400> SEQUENCE: 35

His Gly Glu Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 36
<211> LENGTH: 28
<212> TYPE: PRT
<213> ORGANISM: Artificial Sequence
<220> FEATURE:
<223> OTHER INFORMATION: Exendin Analog 34

<400> SEQUENCE: 36

His Gly Glu Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 37
```

```
<211> LENGTH: 28
<212> TYPE: PRT
<213> ORGANISM: Artificial Sequence
<220> FEATURE:
<223> OTHER INFORMATION: Exendin Analog 35

<400> SEQUENCE: 37

His Gly Glu Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 38
<211> LENGTH: 28
<212> TYPE: PRT
<213> ORGANISM: Artificial Sequence
<220> FEATURE:
<223> OTHER INFORMATION: Exendin Analog 36

<400> SEQUENCE: 38

His Gly Glu Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 39
<211> LENGTH: 28
<212> TYPE: PRT
<213> ORGANISM: Artificial Sequence
<220> FEATURE:
<223> OTHER INFORMATION: Exendin Analog 37

<400> SEQUENCE: 39

His Gly Glu Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 40
<211> LENGTH: 28
<212> TYPE: PRT
<213> ORGANISM: Artificial Sequence
<220> FEATURE:
<223> OTHER INFORMATION: Exendin Analog 38

<400> SEQUENCE: 40

His Gly Glu Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 41
<211> LENGTH: 28
<212> TYPE: PRT
<213> ORGANISM: Artificial Sequence
<220> FEATURE:
<223> OTHER INFORMATION: Exendin Analog 39

<400> SEQUENCE: 41

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25
```

-continued

```
<210> SEQ ID NO 42
<211> LENGTH: 28
<212> TYPE: PRT
<213> ORGANISM: Artificial Sequence
<220> FEATURE:
<223> OTHER INFORMATION: Exendin Analog 40

<400> SEQUENCE: 42

His Gly Glu Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 43
<211> LENGTH: 28
<212> TYPE: PRT
<213> ORGANISM: Artificial Sequence
<220> FEATURE:
<223> OTHER INFORMATION: Exendin Analog 41

<400> SEQUENCE: 43

His Gly Glu Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: Exendin Analog 42

<400> SEQUENCE: 44

His Gly Glu Gly Thr Phe Thr Ser Asp Leu Ser Lys Gln Leu Glu Glu
1               5                   10                  15

Glu Ala Val Arg Leu Phe Ile Ala Phe Leu Lys Asn
            20                  25

<210> SEQ ID NO 45
<211> LENGTH: 28
<212> TYPE: PRT
<213> ORGANISM: Artificial Sequence
<220> FEATURE:
<223> OTHER INFORMATION: Exendin Analog 43

<400> SEQUENCE: 45

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 46
<211> LENGTH: 28
<212> TYPE: PRT
<213> ORGANISM: Artificial Sequence
<220> FEATURE:
<223> OTHER INFORMATION: Exendin Analog 44

<400> SEQUENCE: 46

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25
```

<210> SEQ ID NO 47
<211> LENGTH: 28
<212> TYPE: PRT
<213> ORGANISM: Artificial Sequence
<220> FEATURE:
<223> OTHER INFORMATION: Exendin Analog 45

<400> SEQUENCE: 47

His Gly Glu Gly Thr Phe Thr Ser Asp Leu Ser Lys Gln Leu Glu Glu
1               5                  10                  15

Glu Ala Val Arg Leu Phe Ile Glu Phe Leu Ala Asn
            20                  25

<210> SEQ ID NO 48
<211> LENGTH: 28
<212> TYPE: PRT
<213> ORGANISM: Artificial Sequence
<220> FEATURE:
<223> OTHER INFORMATION: Exendin Analog 46

<400> SEQUENCE: 48

His Gly Glu Gly Thr Phe Thr Ser Asp Leu Ser Lys Gln Leu Glu Glu
1               5                  10                  15

Glu Ala Val Arg Leu Phe Ile Glu Phe Leu Lys Ala
            20                  25

<210> SEQ ID NO 49
<211> LENGTH: 38
<212> TYPE: PRT
<213> ORGANISM: Artificial Sequence
<220> FEATURE:
<223> OTHER INFORMATION: Exendin Analog 47

<400> SEQUENCE: 49

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 50
<211> LENGTH: 38
<212> TYPE: PRT
<213> ORGANISM: Artificial Sequence
<220> FEATURE:
<223> OTHER INFORMATION: Exendin Analog 48

<400> SEQUENCE: 50

His Gly Glu Gly Thr Phe Thr Ser Asp Leu Ser Lys Gln Leu Glu Glu
1               5                  10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 51
<211> LENGTH: 37
<212> TYPE: PRT
<213> ORGANISM: Artificial Sequence
<220> FEATURE:
<223> OTHER INFORMATION: Exendin Analog 49

<400> SEQUENCE: 51

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 52
<211> LENGTH: 37
<212> TYPE: PRT
<213> ORGANISM: Artificial Sequence
<220> FEATURE:
<223> OTHER INFORMATION: Exendin Analog 50

<400> SEQUENCE: 52

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 53
<211> LENGTH: 36
<212> TYPE: PRT
<213> ORGANISM: Artificial Sequence
<220> FEATURE:
<223> OTHER INFORMATION: Exendin Analog 51

<400> SEQUENCE: 53

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 54
<211> LENGTH: 36
<212> TYPE: PRT
<213> ORGANISM: Artificial Sequence
<220> FEATURE:
<223> OTHER INFORMATION: Exendin Analog 52

<400> SEQUENCE: 54

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 55
<211> LENGTH: 35
<212> TYPE: PRT
<213> ORGANISM: Artificial Sequence
<220> FEATURE:
<223> OTHER INFORMATION: Exendin Analog 53

<400> SEQUENCE: 55

His Gly Glu Gly Thr Phe Thr Ser Asp Leu Ser Lys Gln Met Glu Glu
1               5                   10                  15

```
Glu Ala Val Arg Leu Phe Ile Glu Trp Leu Lys Asn Gly Gly Pro Ser
            20                  25                  30

Ser Gly Ala
        35

<210> SEQ ID NO 56
<211> LENGTH: 35
<212> TYPE: PRT
<213> ORGANISM: Artificial Sequence
<220> FEATURE:
<223> OTHER INFORMATION: Exendin Analog 54

<400> SEQUENCE: 56

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 57
<211> LENGTH: 34
<212> TYPE: PRT
<213> ORGANISM: Artificial Sequence
<220> FEATURE:
<223> OTHER INFORMATION: Exendin Analog 55

<400> SEQUENCE: 57

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 58
<211> LENGTH: 34
<212> TYPE: PRT
<213> ORGANISM: Artificial Sequence
<220> FEATURE:
<223> OTHER INFORMATION: Exendin Analog 56

<400> SEQUENCE: 58

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly

<210> SEQ ID NO 59
<211> LENGTH: 33
<212> TYPE: PRT
<213> ORGANISM: Artificial Sequence
<220> FEATURE:
<223> OTHER INFORMATION: Exendin Analog 57

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser
```

<210> SEQ ID NO 60
<211> LENGTH: 33
<212> TYPE: PRT
<213> ORGANISM: Artificial Sequence
<220> FEATURE:
<223> OTHER INFORMATION: Exendin Analog 58

<400> SEQUENCE: 60

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

<210> SEQ ID NO 61
<211> LENGTH: 32
<212> TYPE: PRT
<213> ORGANISM: Artificial Sequence
<220> FEATURE:
<223> OTHER INFORMATION: Exendin Analog 59

<400> SEQUENCE: 61

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Exendin Analog 60

<400> SEQUENCE: 62

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: Exendin Analog 61

<400> SEQUENCE: 63

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Exendin Analog 62

<400> SEQUENCE: 64

His Gly Glu Gly Thr Phe Thr Ser Asp Leu Ser Lys Gln Leu Glu Glu
1               5                   10                  15

-continued

Glu Ala Val Arg Leu Phe Ile Glu Phe Leu Lys Asn Gly Gly Pro
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Exendin Analog 63

<400> SEQUENCE: 65

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 66
<211> LENGTH: 29
<212> TYPE: PRT
<213> ORGANISM: Artificial Sequence
<220> FEATURE:
<223> OTHER INFORMATION: Exendin Analog 64

<400> SEQUENCE: 66

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 67
<211> LENGTH: 29
<212> TYPE: PRT
<213> ORGANISM: Artificial Sequence
<220> FEATURE:
<223> OTHER INFORMATION: Exendin Analog 65

<400> SEQUENCE: 67

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 68
<211> LENGTH: 38
<212> TYPE: PRT
<213> ORGANISM: Artificial Sequence
<220> FEATURE:
<223> OTHER INFORMATION: Exendin Analog 66
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(38)
<223> OTHER INFORMATION: homoproline

<400> SEQUENCE: 68

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa
        35

```
<210> SEQ ID NO 69
<211> LENGTH: 38
<212> TYPE: PRT
<213> ORGANISM: Artificial Sequence
<220> FEATURE:
<223> OTHER INFORMATION: Exendin Analog 67
<220> FEATURE:
<221> NAME/KEY: MOD_RES
<222> LOCATION: (36)..(38)
<223> OTHER INFORMATION: homoproline

<400> SEQUENCE: 69

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 70
<211> LENGTH: 37
<212> TYPE: PRT
<213> ORGANISM: Artificial Sequence
<220> FEATURE:
<223> OTHER INFORMATION: Exendin Analog 68
<220> FEATURE:
<221> NAME/KEY: MOD_RES
<222> LOCATION: (31)..(31)
<223> OTHER INFORMATION: N-methylalanine

<400> SEQUENCE: 70

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Pro Pro
        35

<210> SEQ ID NO 71
<211> LENGTH: 37
<212> TYPE: PRT
<213> ORGANISM: Artificial Sequence
<220> FEATURE:
<223> OTHER INFORMATION: Exendin Analog 69
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(37)
<223> OTHER INFORMATION: N-methylalanine

<400> SEQUENCE: 71

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 72
<211> LENGTH: 37
<212> TYPE: PRT
<213> ORGANISM: Artificial Sequence
<220> FEATURE:
```

-continued

```
<223> OTHER INFORMATION: Exendin Analog 70
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(37)
<223> OTHER INFORMATION: homoproline

<400> SEQUENCE: 72

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 73
<211> LENGTH: 36
<212> TYPE: PRT
<213> ORGANISM: Artificial Sequence
<220> FEATURE:
<223> OTHER INFORMATION: Exendin Analog 71
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(36)
<223> OTHER INFORMATION: homoproline

<400> SEQUENCE: 73

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 74
<211> LENGTH: 35
<212> TYPE: PRT
<213> ORGANISM: Artificial Sequence
<220> FEATURE:
<223> OTHER INFORMATION: Exendin Analog 72

<400> SEQUENCE: 74

Arg Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 75
<211> LENGTH: 30
<212> TYPE: PRT
<213> ORGANISM: Artificial Sequence
<220> FEATURE:
<223> OTHER INFORMATION: Exendin Analog 73

<400> SEQUENCE: 75

His Gly Asp Gly Thr Phe Thr Ser Asp Leu Ser Lys Gln Met Glu Glu
1               5                   10                  15
```

Glu Ala Val Arg Leu Phe Ile Glu Trp Leu Lys Asn Gly Gly
            20                  25                  30

<210> SEQ ID NO 76
<211> LENGTH: 28
<212> TYPE: PRT
<213> ORGANISM: Artificial Sequence
<220> FEATURE:
<223> OTHER INFORMATION: Exendin Analog 74
<220> FEATURE:
<221> NAME/KEY: MOD_RES
<222> LOCATION: (6)..(6)
<223> OTHER INFORMATION: naphthylalanine

<400> SEQUENCE: 76

His Gly Glu Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 77
<211> LENGTH: 28
<212> TYPE: PRT
<213> ORGANISM: Artificial Sequence
<220> FEATURE:
<223> OTHER INFORMATION: Exendin Analog 75

<400> SEQUENCE: 77

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 78
<211> LENGTH: 28
<212> TYPE: PRT
<213> ORGANISM: Artificial Sequence
<220> FEATURE:
<223> OTHER INFORMATION: Exendin Analog 76

<400> SEQUENCE: 78

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn
            20                  25

<210> SEQ ID NO 79
<211> LENGTH: 28
<212> TYPE: PRT
<213> ORGANISM: Artificial Sequence
<220> FEATURE:
<223> OTHER INFORMATION: Exendin Analog 77

<400> SEQUENCE: 79

His Gly Glu Gly Thr Phe Thr Ser Glu Leu Ser Lys Gln Met Ala Glu
1               5                   10                  15

Glu Ala Val Arg Leu Phe Ile Glu Trp Leu Lys Asn
            20                  25

<210> SEQ ID NO 80
<211> LENGTH: 28
<212> TYPE: PRT
<213> ORGANISM: Artificial Sequence
<220> FEATURE:
<223> OTHER INFORMATION: Exendin Analog 78

```
<220> FEATURE:
<221> NAME/KEY: MOD_RES
<222> LOCATION: (10)..(10)
<223> OTHER INFORMATION: pentylglycine

<400> SEQUENCE: 80

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 81
<211> LENGTH: 28
<212> TYPE: PRT
<213> ORGANISM: Artificial Sequence
<220> FEATURE:
<223> OTHER INFORMATION: Exendin Analog 79
<220> FEATURE:
<221> NAME/KEY: MOD_RES
<222> LOCATION: (22)..(22)
<223> OTHER INFORMATION: naphthylalanine

<400> SEQUENCE: 81

His Gly Glu Gly Thr Phe Thr Ser Asp Leu Ser Lys Gln Leu Glu Glu
1               5                   10                  15

Glu Ala Val Arg Leu Xaa Ile Glu Phe Leu Lys Asn
            20                  25

<210> SEQ ID NO 82
<211> LENGTH: 28
<212> TYPE: PRT
<213> ORGANISM: Artificial Sequence
<220> FEATURE:
<223> OTHER INFORMATION: Exendin Analog 80
<220> FEATURE:
<221> NAME/KEY: MOD_RES
<222> LOCATION: (23)..(23)
<223> OTHER INFORMATION: tert-butylglycine

<400> SEQUENCE: 82

His Gly Glu Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 83
<211> LENGTH: 28
<212> TYPE: PRT
<213> ORGANISM: Artificial Sequence
<220> FEATURE:
<223> OTHER INFORMATION: Exendin Analog 81

<400> SEQUENCE: 83

His Gly Glu Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

<210> SEQ ID NO 84
<211> LENGTH: 33
<212> TYPE: PRT
<213> ORGANISM: Artificial Sequence
<220> FEATURE:
<223> OTHER INFORMATION: Exendin Analog 82

<400> SEQUENCE: 84
```

```
His Gly Glu Gly Thr Phe Thr Ser Asp Ala Ser Lys Gln Leu Glu
1               5                   10                  15

Glu Ala Val Arg Leu Phe Ile Glu Phe Leu Lys Asn Gly Gly Pro Ser
            20                  25                  30

Ser
```

<210> SEQ ID NO 85
<211> LENGTH: 29
<212> TYPE: PRT
<213> ORGANISM: Artificial Sequence
<220> FEATURE:
<223> OTHER INFORMATION: Exendin Analog 83

<400> SEQUENCE: 85

```
His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly
            20                  25
```

<210> SEQ ID NO 86
<211> LENGTH: 37
<212> TYPE: PRT
<213> ORGANISM: Artificial Sequence
<220> FEATURE:
<223> OTHER INFORMATION: Exendin Analog 84
<220> FEATURE:
<221> NAME/KEY: MOD_RES
<222> LOCATION: (31)..(31)
<223> OTHER INFORMATION: pentylglycine
<220> FEATURE:
<221> NAME/KEY: MOD_RES
<222> LOCATION: (36)..(37)
<223> OTHER INFORMATION: pentylglycine

<400> SEQUENCE: 86

```
His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35
```

<210> SEQ ID NO 87
<211> LENGTH: 27
<212> TYPE: PRT
<213> ORGANISM: Artificial Sequence
<220> FEATURE:
<223> OTHER INFORMATION: Exendin Analog 85
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: 4-ImidazolylPpionyl-Gly

<400> SEQUENCE: 87

```
Xaa Glu Gly Thr Phe Thr Ser Asp Leu Ser Lys Gln Met Glu Glu
1               5                   10                  15

Ala Val Arg Leu Phe Ile Glu Trp Leu Xaa Asn
            20                  25
```

<210> SEQ ID NO 88
<211> LENGTH: 27
<212> TYPE: PRT

```
<213> ORGANISM: Artificial Sequence
<220> FEATURE:
<223> OTHER INFORMATION: Exendin Analog 86
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: 4-ImidazolylPpionyl-Gly

<400> SEQUENCE: 88

Xaa Glu Gly Thr Phe Thr Ser Asp Leu Ser Lys Gln Leu Glu Glu
1               5                   10                  15

Ala Val Arg Leu Phe Ile Glu Phe Leu Xaa Asn
            20                  25

<210> SEQ ID NO 89
<211> LENGTH: 29
<212> TYPE: PRT
<213> ORGANISM: Artificial Sequence
<220> FEATURE:
<223> OTHER INFORMATION: Exendin Analog 87
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: 4-ImidazolylPpionyl-Gly

<400> SEQUENCE: 89

Xaa Glu Gly Thr Phe Thr Ser Asp Leu Ser Lys Gln Met Glu Glu
1               5                   10                  15

Ala Val Arg Leu Phe Ile Glu Trp Leu Xaa Asn Gly Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: Exendin Analog 88
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: 4-ImidazolylPpionyl-Gly

<400> SEQUENCE: 90

Xaa Glu Gly Thr Phe Thr Ser Asp Leu Ser Lys Gln Leu Glu Glu
1               5                   10                  15

Ala Val Arg Leu Phe Ile Glu Phe Leu Xaa Asn Gly Gly
            20                  25

<210> SEQ ID NO 91
<211> LENGTH: 27
<212> TYPE: PRT
<213> ORGANISM: Artificial Sequence
<220> FEATURE:
<223> OTHER INFORMATION: Exendin Analog 89
<220> FEATURE:
<221> NAME/KEY: MOD_RES
<222> LOCATION: (1)..(1)
<223> OTHER INFORMATION: 4-ImidazolylPpionyl-Gly
```

-continued

```
<220> FEATURE:
<221> NAME/KEY: MOD_RES
<222> LOCATION: (27)..(27)
<223> OTHER INFORMATION: 4-ImidazolylPpionyl-Gly

<400> SEQUENCE: 91

Xaa Glu Gly Thr Phe Thr Ser Asp Leu Ser Lys Gln Met Glu Glu
1               5                   10                  15

Ala Val Arg Leu Phe Ile Glu Trp Leu Asn Xaa
            20                  25

<210> SEQ ID NO 92
<211> LENGTH: 27
<212> TYPE: PRT
<213> ORGANISM: Artificial Sequence
<220> FEATURE:
<223> OTHER INFORMATION: Exendin Analog 90
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: 4-ImidazolylPpionyl-Gly

<400> SEQUENCE: 92

Xaa Glu Gly Thr Phe Thr Ser Asp Leu Ser Lys Gln Leu Glu Glu
1               5                   10                  15

Ala Val Arg Leu Phe Ile Glu Phe Leu Asn Xaa
            20                  25

<210> SEQ ID NO 93
<211> LENGTH: 29
<212> TYPE: PRT
<213> ORGANISM: Artificial Sequence
<220> FEATURE:
<223> OTHER INFORMATION: Exendin Analog 91
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: 4-ImidazolylPpionyl-Gly

<400> SEQUENCE: 93

Xaa Glu Gly Thr Phe Thr Ser Asp Leu Ser Lys Gln Met Glu Glu
1               5                   10                  15

Ala Val Arg Leu Phe Ile Glu Trp Leu Asn Xaa Gly Gly
            20                  25

<210> SEQ ID NO 94
<211> LENGTH: 29
<212> TYPE: PRT
<213> ORGANISM: Artificial Sequence
<220> FEATURE:
<223> OTHER INFORMATION: Exendin Analog 92
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: 4-ImidazolylPpionyl-Gly

<400> SEQUENCE: 94
```

```
Xaa Glu Gly Thr Phe Thr Ser Asp Leu Ser Lys Gln Leu Glu Glu
1               5                   10                  15

Ala Val Arg Leu Phe Ile Glu Phe Leu Asn Xaa Gly Gly
            20                  25
```

<210> SEQ ID NO 95
<211> LENGTH: 28
<212> TYPE: PRT
<213> ORGANISM: Artificial Sequence
<220> FEATURE:
<223> OTHER INFORMATION: Exendin Analog 93

<400> SEQUENCE: 95

```
Ala Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25
```

<210> SEQ ID NO 96
<211> LENGTH: 28
<212> TYPE: PRT
<213> ORGANISM: Artificial Sequence
<220> FEATURE:
<223> OTHER INFORMATION: Exendin Analog 94

<400> SEQUENCE: 96

```
His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25
```

<210> SEQ ID NO 97
<211> LENGTH: 28
<212> TYPE: PRT
<213> ORGANISM: Artificial Sequence
<220> FEATURE:
<223> OTHER INFORMATION: Exendin Analog 95

<400> SEQUENCE: 97

```
His Gly Glu Ala Thr Phe Thr Ser Asp Leu Ser Lys Gln Leu Glu Glu
1               5                   10                  15

Glu Ala Val Arg Leu Phe Ile Glu Phe Leu Lys Asn
            20                  25
```

<210> SEQ ID NO 98
<211> LENGTH: 28
<212> TYPE: PRT
<213> ORGANISM: Artificial Sequence
<220> FEATURE:
<223> OTHER INFORMATION: Exendin Analog 96

<400> SEQUENCE: 98

```
His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25
```

<210> SEQ ID NO 99
<211> LENGTH: 28
<212> TYPE: PRT
<213> ORGANISM: Artificial Sequence
<220> FEATURE:
<223> OTHER INFORMATION: Exendin Analog 97

<400> SEQUENCE: 99

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 100
<211> LENGTH: 28
<212> TYPE: PRT
<213> ORGANISM: Artificial Sequence
<220> FEATURE:
<223> OTHER INFORMATION: Exendin Analog 98

<400> SEQUENCE: 100

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: Exendin Analog 99

<400> SEQUENCE: 101

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Exendin Analog 100

<400> SEQUENCE: 102

His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn
            20                  25

<210> SEQ ID NO 103
<211> LENGTH: 28
<212> TYPE: PRT
<213> ORGANISM: Artificial Sequence
<220> FEATURE:
<223> OTHER INFORMATION: Exendin Analog 101

<400> SEQUENCE: 103

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 104
<211> LENGTH: 28
<212> TYPE: PRT
<213> ORGANISM: Artificial Sequence
<220> FEATURE:
<223> OTHER INFORMATION: Exendin Analog 102

```
<400> SEQUENCE: 104

Ala Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 105
<211> LENGTH: 28
<212> TYPE: PRT
<213> ORGANISM: Artificial Sequence
<220> FEATURE:
<223> OTHER INFORMATION: Exendin Analog 103

<400> SEQUENCE: 105

Ala Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: Exendin Analog 104

<400> SEQUENCE: 106

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 107
<211> LENGTH: 28
<212> TYPE: PRT
<213> ORGANISM: Artificial Sequence
<220> FEATURE:
<223> OTHER INFORMATION: Exendin Analog 105

<400> SEQUENCE: 107

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 108
<211> LENGTH: 28
<212> TYPE: PRT
<213> ORGANISM: Artificial Sequence
<220> FEATURE:
<223> OTHER INFORMATION: Exendin Analog 106

<400> SEQUENCE: 108

Ala Gly Asp Gly Ala Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 109
<211> LENGTH: 28
<212> TYPE: PRT
<213> ORGANISM: Artificial Sequence
<220> FEATURE:
<223> OTHER INFORMATION: Exendin Analog 107
```

```
<400> SEQUENCE: 109

Ala Gly Asp Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 110
<211> LENGTH: 28
<212> TYPE: PRT
<213> ORGANISM: Artificial Sequence
<220> FEATURE:
<223> OTHER INFORMATION: Exendin Analog 108
<220> FEATURE:
<221> NAME/KEY: MOD_RES
<222> LOCATION: (6)..(6)
<223> OTHER INFORMATION: N-methylglycine

<400> SEQUENCE: 110

Ala Gly Asp Gly Thr Xaa Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 111
<211> LENGTH: 28
<212> TYPE: PRT
<213> ORGANISM: Artificial Sequence
<220> FEATURE:
<223> OTHER INFORMATION: Exendin Analog 109
<220> FEATURE:
<221> NAME/KEY: MOD_RES
<222> LOCATION: (6)..(6)
<223> OTHER INFORMATION: N-methylglycine

<400> SEQUENCE: 111

Ala Gly Asp Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 112
<211> LENGTH: 28
<212> TYPE: PRT
<213> ORGANISM: Artificial Sequence
<220> FEATURE:
<223> OTHER INFORMATION: Exendin Analog 110

<400> SEQUENCE: 112

Ala Gly Asp Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 113
<211> LENGTH: 28
<212> TYPE: PRT
<213> ORGANISM: Artificial Sequence
<220> FEATURE:
<223> OTHER INFORMATION: Exendin Analog 111

<400> SEQUENCE: 113

Ala Gly Asp Gly Thr Phe Ser Ser Asp Leu Ser Lys Gln Leu Glu Glu
1               5                   10                  15

Glu Ala Val Arg Leu Phe Ile Glu Phe Leu Lys Asn
```

20                  25

<210> SEQ ID NO 114
<211> LENGTH: 28
<212> TYPE: PRT
<213> ORGANISM: Artificial Sequence
<220> FEATURE:
<223> OTHER INFORMATION: Exendin Analog 112

<400> SEQUENCE: 114

Ala Gly Asp Gly Thr Phe Thr Ala Asp Leu Ser Lys Gln Met Glu Glu
1               5                   10                  15

Glu Ala Val Arg Leu Phe Ile Glu Trp Leu Lys Asn
            20                  25

<210> SEQ ID NO 115
<211> LENGTH: 28
<212> TYPE: PRT
<213> ORGANISM: Artificial Sequence
<220> FEATURE:
<223> OTHER INFORMATION: Exendin Analog 113

<400> SEQUENCE: 115

Ala Gly Asp Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 116
<211> LENGTH: 28
<212> TYPE: PRT
<213> ORGANISM: Artificial Sequence
<220> FEATURE:
<223> OTHER INFORMATION: Exendin Analog 114

<400> SEQUENCE: 116

Ala Gly Asp Gly Thr Phe Thr Ser Ala Leu Ser Lys Gln Met Glu Glu
1               5                   10                  15

Glu Ala Val Arg Leu Phe Ile Glu Trp Leu Lys Asn
            20                  25

<210> SEQ ID NO 117
<211> LENGTH: 28
<212> TYPE: PRT
<213> ORGANISM: Artificial Sequence
<220> FEATURE:
<223> OTHER INFORMATION: Exendin Analog 115

<400> SEQUENCE: 117

Ala Gly Asp Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 118
<211> LENGTH: 28
<212> TYPE: PRT
<213> ORGANISM: Artificial Sequence
<220> FEATURE:
<223> OTHER INFORMATION: Exendin Analog 116

<400> SEQUENCE: 118

Ala Gly Asp Gly Thr Phe Thr Ser Glu Leu Ser Lys Gln Met Glu Glu
1               5                   10                  15

Glu Ala Val Arg Leu Phe Ile Glu Trp Leu Lys Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: Exendin Analog 117

<400> SEQUENCE: 119

Ala Gly Asp Gly Thr Phe Thr Ser Glu Leu Ser Lys Gln Leu Glu Glu
1               5                   10                  15

Glu Ala Val Arg Leu Phe Ile Glu Phe Leu Lys Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Exendin Analog 118

<400> SEQUENCE: 120

Ala Gly Asp Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: Exendin Analog 119

<400> SEQUENCE: 121

Ala Gly Asp Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: Exendin Analog 120
<220> FEATURE:
<221> NAME/KEY: MOD_RES
<222> LOCATION: (10)..(10)
<223> OTHER INFORMATION: pentylglycine

<400> SEQUENCE: 122

Ala Gly Asp Gly Thr Phe Thr Ser Asp Xaa Ser Lys Gln Met Glu Glu
1               5                   10                  15

Glu Ala Val Arg Leu Phe Ile Glu Trp Leu Lys Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Exendin Analog 121
<220> FEATURE:

```
<221> NAME/KEY: MOD_RES
<222> LOCATION: (10)..(10)
<223> OTHER INFORMATION: pentylglycine

<400> SEQUENCE: 123

Ala Gly Asp Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 124
<211> LENGTH: 28
<212> TYPE: PRT
<213> ORGANISM: Artificial Sequence
<220> FEATURE:
<223> OTHER INFORMATION: Exendin Analog 122

<400> SEQUENCE: 124

Ala Gly Asp Gly Thr Phe Thr Ser Asp Leu Ala Lys Gln Met Glu Glu
1               5                   10                  15

Glu Ala Val Arg Leu Phe Ile Glu Trp Leu Lys Asn
            20                  25

<210> SEQ ID NO 125
<211> LENGTH: 28
<212> TYPE: PRT
<213> ORGANISM: Artificial Sequence
<220> FEATURE:
<223> OTHER INFORMATION: Exendin Analog 123

<400> SEQUENCE: 125

Ala Gly Asp Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 126
<211> LENGTH: 28
<212> TYPE: PRT
<213> ORGANISM: Artificial Sequence
<220> FEATURE:
<223> OTHER INFORMATION: Exendin Analog 124

<400> SEQUENCE: 126

Ala Gly Asp Gly Thr Phe Thr Ser Asp Leu Ser Ala Gln Met Glu Glu
1               5                   10                  15

Glu Ala Val Arg Leu Phe Ile Glu Trp Leu Lys Asn
            20                  25

<210> SEQ ID NO 127
<211> LENGTH: 28
<212> TYPE: PRT
<213> ORGANISM: Artificial Sequence
<220> FEATURE:
<223> OTHER INFORMATION: Exendin Analog 125

<400> SEQUENCE: 127

Ala Gly Asp Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 128
<211> LENGTH: 28
```

```
<212> TYPE: PRT
<213> ORGANISM: Artificial Sequence
<220> FEATURE:
<223> OTHER INFORMATION: Exendin Analog 126

<400> SEQUENCE: 128

Ala Gly Asp Gly Thr Phe Thr Ser Asp Leu Ser Lys Ala Met Glu Glu
1               5                   10                  15

Glu Ala Val Arg Leu Phe Ile Glu Trp Leu Lys Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: Exendin Analog 127

<400> SEQUENCE: 129

Ala Gly Asp Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 130
<211> LENGTH: 28
<212> TYPE: PRT
<213> ORGANISM: Artificial Sequence
<220> FEATURE:
<223> OTHER INFORMATION: Exendin Analog 128

<400> SEQUENCE: 130

Ala Gly Asp Gly Thr Phe Thr Ser Asp Leu Ser Lys Gln Ala Glu Glu
1               5                   10                  15

Glu Ala Val Arg Leu Phe Ile Glu Trp Leu Lys Asn
            20                  25

<210> SEQ ID NO 131
<211> LENGTH: 28
<212> TYPE: PRT
<213> ORGANISM: Artificial Sequence
<220> FEATURE:
<223> OTHER INFORMATION: Exendin Analog 129

<400> SEQUENCE: 131

Ala Gly Asp Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: Exendin Analog 130
<220> FEATURE:
<221> NAME/KEY: MOD_RES
<222> LOCATION: (14)..(14)
<223> OTHER INFORMATION: pentylglycine

<400> SEQUENCE: 132

Ala Gly Asp Gly Thr Phe Thr Ser Asp Leu Ser Lys Gln Xaa Glu Glu
1               5                   10                  15

Glu Ala Val Arg Leu Phe Ile Glu Trp Leu Lys Asn
```

20                  25

<210> SEQ ID NO 133
<211> LENGTH: 28
<212> TYPE: PRT
<213> ORGANISM: Artificial Sequence
<220> FEATURE:
<223> OTHER INFORMATION: Exendin Analog 131
<220> FEATURE:
<221> NAME/KEY: MOD_RES
<222> LOCATION: (14)..(14)
<223> OTHER INFORMATION: pentylglycine

<400> SEQUENCE: 133

Ala Gly Asp Gly Thr Phe Thr Ser Asp Leu Ser Lys Gln Xaa Glu Glu
1               5                   10                  15

Glu Ala Val Arg Leu Phe Ile Glu Phe Leu Lys Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: Exendin Analog 132

<400> SEQUENCE: 134

Ala Gly Asp Gly Thr Phe Thr Ser Asp Leu Ser Lys Gln Met Ala Glu
1               5                   10                  15

Glu Ala Val Arg Leu Phe Ile Glu Trp Leu Lys Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Exendin Analog 133

<400> SEQUENCE: 135

Ala Gly Asp Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: Exendin Analog 134

<400> SEQUENCE: 136

Ala Gly Asp Gly Thr Phe Thr Ser Asp Leu Ser Lys Gln Met Glu Ala
1               5                   10                  15

Glu Ala Val Arg Leu Phe Ile Glu Trp Leu Lys Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Exendin Analog 135

<400> SEQUENCE: 137

Ala Gly Asp Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 138
<211> LENGTH: 28
<212> TYPE: PRT
<213> ORGANISM: Artificial Sequence
<220> FEATURE:
<223> OTHER INFORMATION: Exendin Analog 136

<400> SEQUENCE: 138

Ala Gly Asp Gly Thr Phe Thr Ser Asp Leu Ser Lys Gln Met Glu Glu
1               5                   10                  15

Ala Ala Val Arg Leu Phe Ile Glu Trp Leu Lys Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: Exendin Analog 137

<400> SEQUENCE: 139

Ala Gly Asp Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: Exendin Analog 138

<400> SEQUENCE: 140

Ala Gly Asp Gly Thr Phe Thr Ser Asp Leu Ser Lys Gln Met Glu Glu
1               5                   10                  15

Glu Ala Ala Arg Leu Phe Ile Glu Trp Leu Lys Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: Exendin Analog 139

<400> SEQUENCE: 141

Ala Gly Asp Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: Exendin Analog 140

-continued

```
<400> SEQUENCE: 142

Ala Gly Asp Gly Thr Phe Thr Ser Asp Leu Ser Lys Gln Met Glu Glu
1               5                   10                  15

Glu Ala Val Ala Leu Phe Ile Glu Trp Leu Lys Asn
            20                  25

<210> SEQ ID NO 143
<211> LENGTH: 28
<212> TYPE: PRT
<213> ORGANISM: Artificial Sequence
<220> FEATURE:
<223> OTHER INFORMATION: Exendin Analog 141

<400> SEQUENCE: 143

Ala Gly Asp Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: Exendin Analog 142

<400> SEQUENCE: 144

Ala Gly Asp Gly Thr Phe Thr Ser Asp Leu Ser Lys Gln Met Glu Glu
1               5                   10                  15

Glu Ala Val Arg Ala Phe Ile Glu Trp Leu Lys Asn
            20                  25

<210> SEQ ID NO 145
<211> LENGTH: 28
<212> TYPE: PRT
<213> ORGANISM: Artificial Sequence
<220> FEATURE:
<223> OTHER INFORMATION: Exendin Analog 143

<400> SEQUENCE: 145

Ala Gly Asp Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 146
<211> LENGTH: 28
<212> TYPE: PRT
<213> ORGANISM: Artificial Sequence
<220> FEATURE:
<223> OTHER INFORMATION: Exendin Analog 144
<220> FEATURE:
<221> NAME/KEY: MOD_RES
<222> LOCATION: (22)..(22)
<223> OTHER INFORMATION: N-methylglycine

<400> SEQUENCE: 146

Ala Gly Asp Gly Thr Phe Thr Ser Asp Leu Ser Lys Gln Met Glu Glu
1               5                   10                  15

Glu Ala Val Arg Leu Xaa Ile Glu Trp Leu Lys Asn
            20                  25

<210> SEQ ID NO 147
<211> LENGTH: 28
```

```
<212> TYPE: PRT
<213> ORGANISM: Artificial Sequence
<220> FEATURE:
<223> OTHER INFORMATION: Exendin Analog 145
<220> FEATURE:
<221> NAME/KEY: MOD_RES
<222> LOCATION: (22)..(22)
<223> OTHER INFORMATION: N-methylglycine

<400> SEQUENCE: 147

Ala Gly Asp Gly Thr Phe Thr Ser Asp Leu Ser Lys Gln Leu Glu Glu
1               5                   10                  15

Glu Ala Val Arg Leu Xaa Ile Glu Phe Leu Lys Asn
            20                  25

<210> SEQ ID NO 148
<211> LENGTH: 28
<212> TYPE: PRT
<213> ORGANISM: Artificial Sequence
<220> FEATURE:
<223> OTHER INFORMATION: Exendin Analog 146

<400> SEQUENCE: 148

Ala Gly Asp Gly Thr Phe Thr Ser Asp Leu Ser Lys Gln Met Glu Glu
1               5                   10                  15

Glu Ala Val Arg Leu Phe Val Glu Trp Leu Lys Asn
            20                  25

<210> SEQ ID NO 149
<211> LENGTH: 28
<212> TYPE: PRT
<213> ORGANISM: Artificial Sequence
<220> FEATURE:
<223> OTHER INFORMATION: Exendin Analog 147

<400> SEQUENCE: 149

Ala Gly Asp Gly Thr Phe Thr Ser Asp Leu Ser Lys Gln Leu Glu Glu
1               5                   10                  15

Glu Ala Val Arg Leu Phe Val Glu Phe Leu Lys Asn
            20                  25

<210> SEQ ID NO 150
<211> LENGTH: 28
<212> TYPE: PRT
<213> ORGANISM: Artificial Sequence
<220> FEATURE:
<223> OTHER INFORMATION: Exendin Analog 148
<220> FEATURE:
<221> NAME/KEY: MOD_RES
<222> LOCATION: (23)..(23)
<223> OTHER INFORMATION: N-ethylglycine

<400> SEQUENCE: 150

Ala Gly Asp Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 151
<211> LENGTH: 28
<212> TYPE: PRT
<213> ORGANISM: Artificial Sequence
<220> FEATURE:
<223> OTHER INFORMATION: Exendin Analog 149
<220> FEATURE:
<221> NAME/KEY: MOD_RES
<222> LOCATION: (23)..(23)
```

<223> OTHER INFORMATION: N-ethylglycine

<400> SEQUENCE: 151

Ala Gly Asp Gly Thr Phe Thr Ser Asp Leu Ser Lys Gln Leu Glu Glu
1               5                   10                  15

Glu Ala Val Arg Leu Phe Xaa Glu Phe Leu Lys Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: Exendin Analog 150

<400> SEQUENCE: 152

Ala Gly Asp Gly Thr Phe Thr Ser Asp Leu Ser Lys Gln Met Glu Glu
1               5                   10                  15

Glu Ala Val Arg Leu Phe Ile Asp Trp Leu Lys Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: Exendin Analog 151

<400> SEQUENCE: 153

Ala Gly Asp Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

<210> SEQ ID NO 154
<211> LENGTH: 28
<212> TYPE: PRT
<213> ORGANISM: Artificial Sequence
<220> FEATURE:
<223> OTHER INFORMATION: Exendin Analog 152

<400> SEQUENCE: 154

Ala Gly Asp Gly Thr Phe Thr Ser Asp Leu Ser Lys Gln Met Glu Glu
1               5                   10                  15

Glu Ala Val Arg Leu Phe Ile Glu Ala Leu Lys Asn
            20                  25

<210> SEQ ID NO 155
<211> LENGTH: 28
<212> TYPE: PRT
<213> ORGANISM: Artificial Sequence
<220> FEATURE:
<223> OTHER INFORMATION: Exendin Analog 153

<400> SEQUENCE: 155

Ala Gly Asp Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 156
<211> LENGTH: 28
<212> TYPE: PRT
<213> ORGANISM: Artificial Sequence

```
<220> FEATURE:
<223> OTHER INFORMATION: Exendin Analog 154

<400> SEQUENCE: 156

Ala Gly Asp Gly Thr Phe Thr Ser Asp Leu Ser Lys Gln Met Glu Glu
1               5                   10                  15

Glu Ala Val Arg Leu Phe Ile Glu Trp Ala Lys Asn
            20                  25

<210> SEQ ID NO 157
<211> LENGTH: 28
<212> TYPE: PRT
<213> ORGANISM: Artificial Sequence
<220> FEATURE:
<223> OTHER INFORMATION: Exendin Analog 155

<400> SEQUENCE: 157

Ala Gly Asp Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: Exendin Analog 156

<400> SEQUENCE: 158

Ala Gly Asp Gly Thr Phe Thr Ser Asp Leu Ser Lys Gln Met Glu Glu
1               5                   10                  15

Glu Ala Val Arg Leu Phe Ile Glu Trp Leu Ala Asn
            20                  25

<210> SEQ ID NO 159
<211> LENGTH: 28
<212> TYPE: PRT
<213> ORGANISM: Artificial Sequence
<220> FEATURE:
<223> OTHER INFORMATION: Exendin Analog 157

<400> SEQUENCE: 159

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 160
<211> LENGTH: 28
<212> TYPE: PRT
<213> ORGANISM: Artificial Sequence
<220> FEATURE:
<223> OTHER INFORMATION: Exendin Analog 158

<400> SEQUENCE: 160

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Ala
            20                  25

<210> SEQ ID NO 161
<211> LENGTH: 28
<212> TYPE: PRT
```

```
<213> ORGANISM: Artificial Sequence
<220> FEATURE:
<223> OTHER INFORMATION: Exendin Analog 159

<400> SEQUENCE: 161

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 162
<211> LENGTH: 38
<212> TYPE: PRT
<213> ORGANISM: Artificial Sequence
<220> FEATURE:
<223> OTHER INFORMATION: Exendin Analog 160

<400> SEQUENCE: 162

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 163
<211> LENGTH: 38
<212> TYPE: PRT
<213> ORGANISM: Artificial Sequence
<220> FEATURE:
<223> OTHER INFORMATION: Exendin Analog 161

<400> SEQUENCE: 163

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 164
<211> LENGTH: 37
<212> TYPE: PRT
<213> ORGANISM: Artificial Sequence
<220> FEATURE:
<223> OTHER INFORMATION: Exendin Analog 162

<400> SEQUENCE: 164

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 165
<211> LENGTH: 36
<212> TYPE: PRT
<213> ORGANISM: Artificial Sequence
<220> FEATURE:
<223> OTHER INFORMATION: Exendin Analog 163

<400> SEQUENCE: 165
```

His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 166
<211> LENGTH: 36
<212> TYPE: PRT
<213> ORGANISM: Artificial Sequence
<220> FEATURE:
<223> OTHER INFORMATION: Exendin Analog 164

<400> SEQUENCE: 166

Ala Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 167
<211> LENGTH: 35
<212> TYPE: PRT
<213> ORGANISM: Artificial Sequence
<220> FEATURE:
<223> OTHER INFORMATION: Exendin Analog 165

<400> SEQUENCE: 167

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 168
<211> LENGTH: 35
<212> TYPE: PRT
<213> ORGANISM: Artificial Sequence
<220> FEATURE:
<223> OTHER INFORMATION: Exendin Analog 166

<400> SEQUENCE: 168

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 169
<211> LENGTH: 34
<212> TYPE: PRT
<213> ORGANISM: Artificial Sequence
<220> FEATURE:
<223> OTHER INFORMATION: Exendin Analog 167

<400> SEQUENCE: 169

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 170
<211> LENGTH: 32
<212> TYPE: PRT
<213> ORGANISM: Artificial Sequence
<220> FEATURE:
<223> OTHER INFORMATION: Exendin Analog 168

<400> SEQUENCE: 170

His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Exendin Analog 169

<400> SEQUENCE: 171

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Exendin Analog 170

<400> SEQUENCE: 172

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

<210> SEQ ID NO 173
<211> LENGTH: 31
<212> TYPE: PRT
<213> ORGANISM: Artificial Sequence
<220> FEATURE:
<223> OTHER INFORMATION: Exendin Analog 171

<400> SEQUENCE: 173

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Exendin Analog 172

<400> SEQUENCE: 174

```
His Gly Glu Gly Thr Phe Thr Ser Ala Leu Ser Lys Gln Leu Glu
1               5                   10                  15

Glu Ala Val Arg Leu Phe Ile Glu Phe Leu Lys Asn Gly Gly
            20                  25                  30
```

<210> SEQ ID NO 175
<211> LENGTH: 29
<212> TYPE: PRT
<213> ORGANISM: Artificial Sequence
<220> FEATURE:
<223> OTHER INFORMATION: Exendin Analog 173

<400> SEQUENCE: 175

```
Ala Gly Glu Gly Thr Phe Thr Ser Asp Leu Ser Lys Gln Leu Glu
1               5                   10                  15

Glu Ala Val Arg Leu Phe Ile Glu Phe Leu Lys Asn Gly
            20                  25
```

<210> SEQ ID NO 176
<211> LENGTH: 38
<212> TYPE: PRT
<213> ORGANISM: Artificial Sequence
<220> FEATURE:
<223> OTHER INFORMATION: Exendin Analog 174
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(38)
<223> OTHER INFORMATION: thioproline

<400> SEQUENCE: 176

```
His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa
        35
```

<210> SEQ ID NO 177
<211> LENGTH: 38
<212> TYPE: PRT
<213> ORGANISM: Artificial Sequence
<220> FEATURE:
<223> OTHER INFORMATION: Exendin Analog 175
<220> FEATURE:
<221> NAME/KEY: MOD_RES
<222> LOCATION: (36)..(38)
<223> OTHER INFORMATION: thioproline

<400> SEQUENCE: 177

```
His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa
        35
```

<210> SEQ ID NO 178
<211> LENGTH: 37
<212> TYPE: PRT
<213> ORGANISM: Artificial Sequence
<220> FEATURE:
<223> OTHER INFORMATION: Exendin Analog 176

```
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(37)
<223> OTHER INFORMATION: N-methylalanine

<400> SEQUENCE: 178

His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 179
<211> LENGTH: 36
<212> TYPE: PRT
<213> ORGANISM: Artificial Sequence
<220> FEATURE:
<223> OTHER INFORMATION: Exendin Analog 177
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(36)
<223> OTHER INFORMATION: thioproline

<400> SEQUENCE: 179

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 180
<211> LENGTH: 35
<212> TYPE: PRT
<213> ORGANISM: Artificial Sequence
<220> FEATURE:
<223> OTHER INFORMATION: Exendin Analog 178

<400> SEQUENCE: 180

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 181
<211> LENGTH: 30
<212> TYPE: PRT
<213> ORGANISM: Artificial Sequence
<220> FEATURE:
<223> OTHER INFORMATION: Exendin Analog 179

<400> SEQUENCE: 181

His Gly Asp Ala Thr Phe Thr Ser Asp Leu Ser Lys Gln Met Glu Glu
1               5                   10                  15
```

Glu Ala Val Arg Leu Phe Ile Glu Trp Leu Lys Asn Gly Gly
            20                  25                  30

<210> SEQ ID NO 182
<211> LENGTH: 39
<212> TYPE: PRT
<213> ORGANISM: Artificial Sequence
<220> FEATURE:
<223> OTHER INFORMATION: Exendin Analog 180

<400> SEQUENCE: 182

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 183
<211> LENGTH: 39
<212> TYPE: PRT
<213> ORGANISM: Artificial Sequence
<220> FEATURE:
<223> OTHER INFORMATION: Exendin Analog 181

<400> SEQUENCE: 183

Ala Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 184
<211> LENGTH: 27
<212> TYPE: PRT
<213> ORGANISM: Artificial Sequence
<220> FEATURE:
<223> OTHER INFORMATION: Exendin Analog 182
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: Lys-NH(epsilon)octanoyl

<400> SEQUENCE: 184

Xaa Glu Gly Thr Phe Thr Ser Ala Leu Ser Lys Gln Met Glu Glu Glu
1               5                   10                  15

Ala Val Arg Leu Phe Ile Glu Trp Leu Xaa Asn
            20                  25

<210> SEQ ID NO 185
<211> LENGTH: 27
<212> TYPE: PRT
<213> ORGANISM: Artificial Sequence
<220> FEATURE:
<223> OTHER INFORMATION: Exendin Analog 183
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)

<223> OTHER INFORMATION: Lys-NH(epsilon)octanoyl

<400> SEQUENCE: 185

Xaa Glu Gly Thr Phe Thr Ser Ala Leu Ser Lys Gln Leu Glu Glu Glu
1               5                   10                  15

Ala Val Arg Leu Phe Ile Glu Phe Leu Xaa Asn
            20                  25

<210> SEQ ID NO 186
<211> LENGTH: 29
<212> TYPE: PRT
<213> ORGANISM: Artificial Sequence
<220> FEATURE:
<223> OTHER INFORMATION: Exendin Analog 184
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: Lys-NH(epsilon)octanoyl

<400> SEQUENCE: 186

Xaa Glu Gly Thr Phe Thr Ser Ala Leu Ser Lys Gln Met Glu Glu Glu
1               5                   10                  15

Ala Val Arg Leu Phe Ile Glu Trp Leu Xaa Asn Gly Gly
            20                  25

<210> SEQ ID NO 187
<211> LENGTH: 29
<212> TYPE: PRT
<213> ORGANISM: Artificial Sequence
<220> FEATURE:
<223> OTHER INFORMATION: Exendin Analog 185
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (26)..(26)
<223> OTHER INFORMATION: Lys-NH(epsilon)octanoyl

<400> SEQUENCE: 187

Xaa Glu Gly Thr Phe Thr Ser Ala Leu Ser Lys Gln Leu Glu Glu Glu
1               5                   10                  15

Ala Val Arg Leu Phe Ile Glu Phe Leu Xaa Asn Gly Gly
            20                  25

<210> SEQ ID NO 188
<211> LENGTH: 27
<212> TYPE: PRT
<213> ORGANISM: Artificial Sequence
<220> FEATURE:
<223> OTHER INFORMATION: Exendin Analog 186
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 188

Xaa Glu Gly Thr Phe Thr Ser Ala Leu Ser Lys Gln Met Glu Glu Glu
1               5                   10                  15

Ala Val Arg Leu Phe Ile Glu Trp Leu Asn Xaa
            20                  25

<210> SEQ ID NO 189
<211> LENGTH: 27
<212> TYPE: PRT
<213> ORGANISM: Artificial Sequence
<220> FEATURE:
<223> OTHER INFORMATION: Exendin Analog 187
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 189

Xaa Glu Gly Thr Phe Thr Ser Ala Leu Ser Lys Gln Leu Glu Glu Glu
1               5                   10                  15

Ala Val Arg Leu Phe Ile Glu Phe Leu Asn Xaa
            20                  25

<210> SEQ ID NO 190
<211> LENGTH: 29
<212> TYPE: PRT
<213> ORGANISM: Artificial Sequence
<220> FEATURE:
<223> OTHER INFORMATION: Exendin Analog 188
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 190

Xaa Glu Gly Thr Phe Thr Ser Ala Leu Ser Lys Gln Met Glu Glu Glu
1               5                   10                  15

Ala Val Arg Leu Phe Ile Glu Trp Leu Asn Xaa Gly Gly
            20                  25

<210> SEQ ID NO 191
<211> LENGTH: 29
<212> TYPE: PRT
<213> ORGANISM: Artificial Sequence
<220> FEATURE:
<223> OTHER INFORMATION: Exendin Analog 189
<220> FEATURE:
<221> NAME/KEY: MOD_RES
<222> LOCATION: (1)..(1)
<223> OTHER INFORMATION: 4-ImidazolylPpionyl-Gly
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 191

Xaa Glu Gly Thr Phe Thr Ser Ala Leu Ser Lys Gln Leu Glu Glu Glu
1               5                   10                  15

Ala Val Arg Leu Phe Ile Glu Phe Leu Asn Xaa Gly Gly
            20                  25

<210> SEQ ID NO 192
<211> LENGTH: 28
<212> TYPE: PRT

<213> ORGANISM: Artificial Sequence
<220> FEATURE:
<223> OTHER INFORMATION: Exendin Analog 190
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 192

Ala Gly Glu Gly Thr Phe Thr Ser Asp Leu Ser Lys Gln Met Glu Glu
1               5                   10                  15

Glu Ala Val Arg Leu Phe Ile Glu Trp Leu Xaa Asn
            20                  25

<210> SEQ ID NO 193
<211> LENGTH: 28
<212> TYPE: PRT
<213> ORGANISM: Artificial Sequence
<220> FEATURE:
<223> OTHER INFORMATION: Exendin Analog 191
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 193

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Xaa Asn
            20                  25

<210> SEQ ID NO 194
<211> LENGTH: 30
<212> TYPE: PRT
<213> ORGANISM: Artificial Sequence
<220> FEATURE:
<223> OTHER INFORMATION: Exendin Analog 192
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 194

Ala Gly Glu Gly Thr Phe Thr Ser Asp Leu Ser Lys Gln Met Glu Glu
1               5                   10                  15

Glu Ala Val Arg Leu Phe Ile Glu Trp Leu Xaa Asn Gly Gly
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Exendin Analog 193
<220> FEATURE:
<221> NAME/KEY: MOD_RES
<222> LOCATION: (27)..(27)
<223> OTHER INFORMATION: Lys-NH(epsilon)octanoyl

<400> SEQUENCE: 195

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Xaa Asn Gly Gly
            20                  25                  30

<210> SEQ ID NO 196
<211> LENGTH: 28

```
<212> TYPE: PRT
<213> ORGANISM: Artificial Sequence
<220> FEATURE:
<223> OTHER INFORMATION: Exendin Analog 194
<220> FEATURE:
<221> NAME/KEY: MOD_RES
<222> LOCATION: (28)..(28)
<223> OTHER INFORMATION: Lys-NH(epsilon)octanoyl

<400> SEQUENCE: 196

Ala Gly Glu Gly Thr Phe Thr Ser Asp Leu Ser Lys Gln Met Glu Glu
1               5                   10                  15

Glu Ala Val Arg Leu Phe Ile Glu Trp Leu Asn Xaa
            20                  25

<210> SEQ ID NO 197
<211> LENGTH: 28
<212> TYPE: PRT
<213> ORGANISM: Artificial Sequence
<220> FEATURE:
<223> OTHER INFORMATION: Exendin Analog 195
<220> FEATURE:
<221> NAME/KEY: MOD_RES
<222> LOCATION: (28)..(28)
<223> OTHER INFORMATION: Lys-NH(epsilon)octanoyl

<400> SEQUENCE: 197

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Asn Xaa
            20                  25

<210> SEQ ID NO 198
<211> LENGTH: 30
<212> TYPE: PRT
<213> ORGANISM: Artificial Sequence
<220> FEATURE:
<223> OTHER INFORMATION: Exendin Analog 196
<220> FEATURE:
<221> NAME/KEY: MOD_RES
<222> LOCATION: (28)..(28)
<223> OTHER INFORMATION: Lys-NH(epsilon)octanoyl

<400> SEQUENCE: 198

Ala Gly Glu Gly Thr Phe Thr Ser Asp Leu Ser Lys Gln Met Glu Glu
1               5                   10                  15

Glu Ala Val Arg Leu Phe Ile Glu Trp Leu Asn Xaa Gly Gly
            20                  25                  30

<210> SEQ ID NO 199
<211> LENGTH: 30
<212> TYPE: PRT
<213> ORGANISM: Artificial Sequence
<220> FEATURE:
<223> OTHER INFORMATION: Exendin Analog 197
<220> FEATURE:
<221> NAME/KEY: MOD_RES
<222> LOCATION: (28)..(28)
<223> OTHER INFORMATION: Lys-NH(epsilon)octanoyl

<400> SEQUENCE: 199

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Asn Xaa Gly Gly
            20                  25                  30

<210> SEQ ID NO 200
```

```
<211> LENGTH: 39
<212> TYPE: PRT
<213> ORGANISM: Artificial Sequence
<220> FEATURE:
<223> OTHER INFORMATION: Exendin Analog 198
<220> FEATURE:
<221> NAME/KEY: misc_feature
<222> LOCATION: (12)..(12)
<223> OTHER INFORMATION: Lys is Pegylated

<400> SEQUENCE: 200

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 201
<211> LENGTH: 39
<212> TYPE: PRT
<213> ORGANISM: Artificial Sequence
<220> FEATURE:
<223> OTHER INFORMATION: Exendin Analog 199
<220> FEATURE:
<221> NAME/KEY: misc_feature
<222> LOCATION: (27)..(27)
<223> OTHER INFORMATION: Lys is Pegylated

<400> SEQUENCE: 201

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 202
<211> LENGTH: 39
<212> TYPE: PRT
<213> ORGANISM: Artificial Sequence
<220> FEATURE:
<223> OTHER INFORMATION: Exendin Analog 200
<220> FEATURE:
<221> NAME/KEY: misc_feature
<222> LOCATION: (2)..(2)
<223> OTHER INFORMATION: Lys is Pegylated

<400> SEQUENCE: 202

His Lys Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 203
<211> LENGTH: 39
<212> TYPE: PRT
<213> ORGANISM: Artificial Sequence
<220> FEATURE:
<223> OTHER INFORMATION: Exendin Analog 201
<220> FEATURE:
<221> NAME/KEY: misc_feature
<222> LOCATION: (5)..(5)
<223> OTHER INFORMATION: Lys is Pegylated
```

-continued

<400> SEQUENCE: 203

His Gly Glu Gly Lys Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 204
<211> LENGTH: 39
<212> TYPE: PRT
<213> ORGANISM: Artificial Sequence
<220> FEATURE:
<223> OTHER INFORMATION: Exendin Analog 202
<220> FEATURE:
<221> NAME/KEY: misc_feature
<222> LOCATION: (8)..(8)
<223> OTHER INFORMATION: Lys is Pegylated

<400> SEQUENCE: 204

His Gly Glu Gly Thr Phe Thr Lys Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 205
<211> LENGTH: 39
<212> TYPE: PRT
<213> ORGANISM: Artificial Sequence
<220> FEATURE:
<223> OTHER INFORMATION: Exendin Analog 203
<220> FEATURE:
<221> NAME/KEY: misc_feature
<222> LOCATION: (10)..(10)
<223> OTHER INFORMATION: Lys is Pegylated

<400> SEQUENCE: 205

His Gly Glu Gly Thr Phe Thr Ser Asp Lys Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 206
<211> LENGTH: 38
<212> TYPE: PRT
<213> ORGANISM: Artificial Sequence
<220> FEATURE:
<223> OTHER INFORMATION: Exendin Analog 204
<220> FEATURE:
<221> NAME/KEY: misc_feature
<222> LOCATION: (11)..(11)
<223> OTHER INFORMATION: Lys is Pegylated

<400> SEQUENCE: 206

His Gly Glu Gly Thr Phe Thr Ser Asp Leu Lys Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Ser
        35

<210> SEQ ID NO 207
<211> LENGTH: 39
<212> TYPE: PRT
<213> ORGANISM: Artificial Sequence
<220> FEATURE:
<223> OTHER INFORMATION: Exendin Analog 205
<220> FEATURE:
<221> NAME/KEY: misc_feature
<222> LOCATION: (13)..(13)
<223> OTHER INFORMATION: Lys is Pegylated

<400> SEQUENCE: 207

His Gly Glu Gly Thr Phe Thr Ser Asp Leu Ser Lys Lys Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 208
<211> LENGTH: 39
<212> TYPE: PRT
<213> ORGANISM: Artificial Sequence
<220> FEATURE:
<223> OTHER INFORMATION: Exendin Analog 206
<220> FEATURE:
<221> NAME/KEY: misc_feature
<222> LOCATION: (16)..(16)
<223> OTHER INFORMATION: Lys is Pegylated

<400> SEQUENCE: 208

His Gly Glu Gly Thr Phe Thr Ser Asp Leu Ser Lys Gln Met Glu Lys
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 209
<211> LENGTH: 39
<212> TYPE: PRT
<213> ORGANISM: Artificial Sequence
<220> FEATURE:
<223> OTHER INFORMATION: Exendin Analog 207
<220> FEATURE:
<221> NAME/KEY: misc_feature
<222> LOCATION: (17)..(17)
<223> OTHER INFORMATION: Lys is Pegylated

<400> SEQUENCE: 209

His Gly Glu Gly Thr Phe Thr Ser Asp Leu Ser Lys Gln Met Glu Glu
1               5                   10                  15

Lys Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 210
<211> LENGTH: 39
<212> TYPE: PRT
<213> ORGANISM: Artificial Sequence
<220> FEATURE:
<223> OTHER INFORMATION: Exendin Analog 208
<220> FEATURE:
<221> NAME/KEY: misc_feature
<222> LOCATION: (19)..(19)
<223> OTHER INFORMATION: Lys is Pegylated

<400> SEQUENCE: 210

His Gly Glu Gly Thr Phe Thr Ser Asp Leu Ser Lys Gln Met Glu Glu
1               5                   10                  15

Glu Ala Lys Arg Leu Phe Ile Glu Trp Leu Lys Asn Gly Gly Pro Ser
            20                  25                  30

Ser Gly Ala Pro Pro Pro Ser
        35

<210> SEQ ID NO 211
<211> LENGTH: 39
<212> TYPE: PRT
<213> ORGANISM: Artificial Sequence
<220> FEATURE:
<223> OTHER INFORMATION: Exendin Analog 209
<220> FEATURE:
<221> NAME/KEY: misc_feature
<222> LOCATION: (27)..(27)
<223> OTHER INFORMATION: Lys is Pegylated

<400> SEQUENCE: 211

His Gly Glu Gly Thr Phe Thr Ser Asp Leu Ser Lys Gln Met Glu Glu
1               5                   10                  15

Glu Ala Val Arg Ser Phe Ile Glu Trp Leu Lys Asn Gly Gly Pro Ser
            20                  25                  30

Ser Gly Ala Pro Pro Pro Ser
        35

<210> SEQ ID NO 212
<211> LENGTH: 39
<212> TYPE: PRT
<213> ORGANISM: Artificial Sequence
<220> FEATURE:
<223> OTHER INFORMATION: Exendin Analog 210
<220> FEATURE:
<221> NAME/KEY: misc_feature
<222> LOCATION: (24)..(24)
<223> OTHER INFORMATION: Lys is Pegylated

<400> SEQUENCE: 212

His Gly Glu Gly Thr Phe Thr Ser Asp Leu Ser Lys Gln Met Glu Glu
1               5                   10                  15

Glu Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 213
<211> LENGTH: 39
<212> TYPE: PRT
<213> ORGANISM: Artificial Sequence
<220> FEATURE:
<223> OTHER INFORMATION: Exendin Analog 211
<220> FEATURE:
<221> NAME/KEY: misc_feature
<222> LOCATION: (25)..(25)
<223> OTHER INFORMATION: Lys is Pegylated

<400> SEQUENCE: 213

His Gly Glu Gly Thr Phe Thr Ser Asp Leu Ser Lys Gln Met Glu Glu
1               5                   10                  15

Glu Ala Val Arg Leu Phe Ile Glu Lys Leu Lys Asn Gly Gly Pro Ser
            20                  25                  30

Ser Gly Ala Pro Pro Pro Ser
        35

<210> SEQ ID NO 214
<211> LENGTH: 39
<212> TYPE: PRT
<213> ORGANISM: Artificial Sequence
<220> FEATURE:
<223> OTHER INFORMATION: Exendin Analog 212
<220> FEATURE:
<221> NAME/KEY: misc_feature
<222> LOCATION: (28)..(28)
<223> OTHER INFORMATION: Lys is Pegylated

<400> SEQUENCE: 214

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 215
<211> LENGTH: 39
<212> TYPE: PRT
<213> ORGANISM: Artificial Sequence
<220> FEATURE:
<223> OTHER INFORMATION: Exendin Analog 213
<220> FEATURE:
<221> NAME/KEY: misc_feature
<222> LOCATION: (29)..(29)
<223> OTHER INFORMATION: Lys is Pegylated

<400> SEQUENCE: 215

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Lys Gly Pro Ser
            20                  25                  30

Ser Gly Ala Pro Pro Pro Ser
        35

<210> SEQ ID NO 216
<211> LENGTH: 39
<212> TYPE: PRT
<213> ORGANISM: Artificial Sequence
<220> FEATURE:
<223> OTHER INFORMATION: Exendin Analog 214
<220> FEATURE:
<221> NAME/KEY: misc_feature
<222> LOCATION: (30)..(30)
<223> OTHER INFORMATION: Lys is Pegylated

<400> SEQUENCE: 216

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Lys Pro Ser
            20                  25                  30

Ser Gly Ala Pro Pro Pro Ser
        35

<210> SEQ ID NO 217
<211> LENGTH: 39
<212> TYPE: PRT
<213> ORGANISM: Artificial Sequence
<220> FEATURE:

```
<223> OTHER INFORMATION: Exendin Analog 215
<220> FEATURE:
<221> NAME/KEY: misc_feature
<222> LOCATION: (1)..(1)
<223> OTHER INFORMATION: His is Acylated

<400> SEQUENCE: 217

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 218
<211> LENGTH: 39
<212> TYPE: PRT
<213> ORGANISM: Artificial Sequence
<220> FEATURE:
<223> OTHER INFORMATION: Exendin Analog 216
<220> FEATURE:
<221> NAME/KEY: misc_feature
<222> LOCATION: (1)..(1)
<223> OTHER INFORMATION: His is Alkylated

<400> SEQUENCE: 218

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 219
<211> LENGTH: 39
<212> TYPE: PRT
<213> ORGANISM: Artificial Sequence
<220> FEATURE:
<223> OTHER INFORMATION: Exendin Analog 217
<220> FEATURE:
<221> NAME/KEY: misc_feature
<222> LOCATION: (27)..(27)
<223> OTHER INFORMATION: Lys is Pegylated

<400> SEQUENCE: 219

His Gly Glu Gly Thr Phe Thr Ser Asp Leu Ser Arg Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 220
<211> LENGTH: 39
<212> TYPE: PRT
<213> ORGANISM: Artificial Sequence
<220> FEATURE:
<223> OTHER INFORMATION: Exendin Analog 218
<220> FEATURE:
<221> NAME/KEY: misc_feature
<222> LOCATION: (12)..(12)
<223> OTHER INFORMATION: Lys is Pegylated

<400> SEQUENCE: 220

His Gly Glu Gly Thr Phe Thr Ser Asp Leu Ser Lys Gln Met Glu Glu
 1               5                  10                  15
```

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 221
<211> LENGTH: 39
<212> TYPE: PRT
<213> ORGANISM: Artificial Sequence
<220> FEATURE:
<223> OTHER INFORMATION: Exendin Analog 219

<400> SEQUENCE: 221

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 222
<211> LENGTH: 39
<212> TYPE: PRT
<213> ORGANISM: Artificial Sequence
<220> FEATURE:
<223> OTHER INFORMATION: Exendin Analog 220
<220> FEATURE:
<221> NAME/KEY: misc_feature
<222> LOCATION: (39)..(39)
<223> OTHER INFORMATION: Lys is Pegylated

<400> SEQUENCE: 222

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Lys
        35

<210> SEQ ID NO 223
<211> LENGTH: 39
<212> TYPE: PRT
<213> ORGANISM: Artificial Sequence
<220> FEATURE:
<223> OTHER INFORMATION: Exendin Analog 221
<220> FEATURE:
<221> NAME/KEY: misc_feature
<222> LOCATION: (30)..(30)
<223> OTHER INFORMATION: Lys is Pegylated

<400> SEQUENCE: 223

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Lys Pro Ser
            20                  25                  30

Ser Gly Ala Pro Pro Pro Ser
        35

<210> SEQ ID NO 224
<211> LENGTH: 39
<212> TYPE: PRT
<213> ORGANISM: Artificial Sequence
<220> FEATURE:
<223> OTHER INFORMATION: Exendin Analog 222

```
<220> FEATURE:
<221> NAME/KEY: misc_feature
<222> LOCATION: (27)..(27)
<223> OTHER INFORMATION: Lys is Pegylated

<400> SEQUENCE: 224

His Gly Glu Gly Thr Phe Thr Ser Asp Leu Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 225
<211> LENGTH: 39
<212> TYPE: PRT
<213> ORGANISM: Artificial Sequence
<220> FEATURE:
<223> OTHER INFORMATION: Exendin Analog 223
<220> FEATURE:
<221> NAME/KEY: misc_feature
<222> LOCATION: (12)..(12)
<223> OTHER INFORMATION: Lys is Pegylated

<400> SEQUENCE: 225

His Gly Glu Gly Thr Phe Thr Ser Asp Leu Ser Lys Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 226
<211> LENGTH: 39
<212> TYPE: PRT
<213> ORGANISM: Artificial Sequence
<220> FEATURE:
<223> OTHER INFORMATION: Exendin Analog 224
<220> FEATURE:
<221> NAME/KEY: misc_feature
<222> LOCATION: (1)..(1)
<223> OTHER INFORMATION: His is Pegylated

<400> SEQUENCE: 226

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Pro Ser
        35

<210> SEQ ID NO 227
<211> LENGTH: 39
<212> TYPE: PRT
<213> ORGANISM: Artificial Sequence
<220> FEATURE:
<223> OTHER INFORMATION: Exendin Analog 225
<220> FEATURE:
<221> NAME/KEY: misc_feature
<222> LOCATION: (1)..(1)
<223> OTHER INFORMATION: His is Pegylated

<400> SEQUENCE: 227

His Gly Glu Gly Thr Phe Thr Ser Asp Leu Ser Arg Gln Met Glu Glu
1               5                   10                  15
```

Glu Ala Val Arg Leu Phe Ile Glu Trp Leu Arg Asn Gly Gly Pro Ser
            20                  25                  30

Ser Gly Ala Pro Pro Ser
        35

<210> SEQ ID NO 228
<211> LENGTH: 39
<212> TYPE: PRT
<213> ORGANISM: Artificial Sequence
<220> FEATURE:
<223> OTHER INFORMATION: Exendin Analog 226
<220> FEATURE:
<221> NAME/KEY: misc_feature
<222> LOCATION: (39)..(39)
<223> OTHER INFORMATION: Lys is Pegylated

<400> SEQUENCE: 228

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Gly Pro Ser
            20                  25                  30

Ser Gly Ala Pro Pro Lys
        35

<210> SEQ ID NO 229
<211> LENGTH: 39
<212> TYPE: PRT
<213> ORGANISM: Artificial Sequence
<220> FEATURE:
<223> OTHER INFORMATION: Exendin Analog 227
<220> FEATURE:
<221> NAME/KEY: misc_feature
<222> LOCATION: (30)..(30)
<223> OTHER INFORMATION: Lys is Pegylated

<400> SEQUENCE: 229

His Gly Glu Gly Thr Phe Thr Ser Asp Leu Ser Arg Gln Met Glu Glu
1               5                   10                  15

Glu Ala Val Arg Leu Phe Ile Glu Trp Leu Arg Asn Gly Lys Pro Ser
            20                  25                  30

Ser Gly Ala Pro Pro Ser
        35

<210> SEQ ID NO 230
<211> LENGTH: 39
<212> TYPE: PRT
<213> ORGANISM: Artificial Sequence
<220> FEATURE:
<223> OTHER INFORMATION: Exendin Analog 228

<400> SEQUENCE: 230

His Gly Glu Gly Thr Phe Thr Ser Asp Leu Ser Lys Gln Arg Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 231
<211> LENGTH: 39
<212> TYPE: PRT
<213> ORGANISM: Artificial Sequence
<220> FEATURE:
<223> OTHER INFORMATION: Exendin Analog 229

```
<400> SEQUENCE: 231

His Gly Glu Gly Thr Phe Thr Ser Asp Leu Ser Lys Gln Arg Glu Glu
1               5                   10                  15

Glu Ala Val His Leu Phe Ile Glu Trp Leu Lys Asn Gly Gly Pro Ser
            20                  25                  30

Ser Gly Ala Pro Pro Ser
        35

<210> SEQ ID NO 232
<211> LENGTH: 39
<212> TYPE: PRT
<213> ORGANISM: Artificial Sequence
<220> FEATURE:
<223> OTHER INFORMATION: Exendin Analog 230

<400> SEQUENCE: 232

His Gly Glu Gly Thr Phe Thr Ser Asp Leu Ser Lys Gln Arg Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
        35

<210> SEQ ID NO 233
<211> LENGTH: 40
<212> TYPE: PRT
<213> ORGANISM: Artificial Sequence
<220> FEATURE:
<223> OTHER INFORMATION: Exendin Analog 231

<400> SEQUENCE: 233

His Gly Glu Gly Thr Phe Thr Ser Asp Leu Ser Lys Gln Arg Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Arg
        35                  40

<210> SEQ ID NO 234
<211> LENGTH: 39
<212> TYPE: PRT
<213> ORGANISM: Artificial Sequence
<220> FEATURE:
<223> OTHER INFORMATION: Exendin Analog 232

<400> SEQUENCE: 234

His Gly Glu Gly Thr Phe Thr Ser Asp Leu Ser Lys Gln Arg Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 235
<211> LENGTH: 40
<212> TYPE: PRT
<213> ORGANISM: Artificial Sequence
<220> FEATURE:
<223> OTHER INFORMATION: Exendin Analog 233

<400> SEQUENCE: 235

His Gly Glu Gly Thr Phe Thr Ser Asp Leu Ser Lys Gln Arg Glu Glu
```

```
                1               5                  10                  15
Glu Ala Val Arg Leu Phe Ile Glu Trp Leu Lys Asn Gly Gly Pro Ser
                20                  25                  30

Ser Gly Ala Pro Pro Ser Lys
        35                  40

<210> SEQ ID NO 236
<211> LENGTH: 40
<212> TYPE: PRT
<213> ORGANISM: Artificial Sequence
<220> FEATURE:
<223> OTHER INFORMATION: Exendin Analog 234

<400> SEQUENCE: 236

His Gly Glu Gly Thr Phe Thr Ser Asp Leu Ser Lys Gln Arg Glu Glu
1               5                  10                  15

Glu Ala Val His Leu Phe Ile Glu Trp Leu Lys Asn Gly Gly Pro Ser
                20                  25                  30

Ser Gly Ala Pro Pro Pro Ser Arg
        35                  40

<210> SEQ ID NO 237
<211> LENGTH: 39
<212> TYPE: PRT
<213> ORGANISM: Artificial Sequence
<220> FEATURE:
<223> OTHER INFORMATION: Exendin Analog 235

<400> SEQUENCE: 237

His Gly Glu Gly Thr Phe Thr Ser Asp Leu Ser Lys Gln Arg Glu Glu
1               5                  10                  15

Glu Ala Val His Leu Phe Ile Glu Trp Leu Lys Asn Gly Gly Pro Ser
                20                  25                  30

Ser Gly Ala Pro Pro Pro Ser
        35

<210> SEQ ID NO 238
<211> LENGTH: 40
<212> TYPE: PRT
<213> ORGANISM: Artificial Sequence
<220> FEATURE:
<223> OTHER INFORMATION: Exendin Analog 236

<400> SEQUENCE: 238

His Gly Glu Gly Thr Phe Thr Ser Asp Leu Ser Lys Gln Arg Glu Glu
1               5                  10                  15

Glu Ala Val His Leu Phe Ile Glu Trp Leu Lys Asn Gly Gly Pro Ser
                20                  25                  30

Ser Gly Ala Pro Pro Pro Ser Lys
        35                  40

<210> SEQ ID NO 239
<211> LENGTH: 40
<212> TYPE: PRT
<213> ORGANISM: Artificial Sequence
<220> FEATURE:
<223> OTHER INFORMATION: Exendin Analog 237

<400> SEQUENCE: 239

His Gly Glu Gly Thr Phe Thr Ser Asp Leu Ser Lys Gln Arg Glu Glu
1               5                  10                  15

Glu Ala Val Lys Leu Phe Ile Glu Trp Leu Lys Asn Gly Gly Pro Ser
```

20                  25                  30

Ser Gly Ala Pro Pro Ser Arg
        35                  40

<210> SEQ ID NO 240
<211> LENGTH: 39
<212> TYPE: PRT
<213> ORGANISM: Artificial Sequence
<220> FEATURE:
<223> OTHER INFORMATION: Exendin Analog 238

<400> SEQUENCE: 240

His Gly Glu Gly Thr Phe Thr Ser Asp Leu Ser Lys Gln Arg Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 241
<211> LENGTH: 40
<212> TYPE: PRT
<213> ORGANISM: Artificial Sequence
<220> FEATURE:
<223> OTHER INFORMATION: Exendin Analog 239

<400> SEQUENCE: 241

His Gly Glu Gly Thr Phe Thr Ser Asp Leu Ser Lys Gln Arg Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser Lys
        35                  40

<210> SEQ ID NO 242
<211> LENGTH: 39
<212> TYPE: PRT
<213> ORGANISM: Artificial Sequence
<220> FEATURE:
<223> OTHER INFORMATION: Exendin Analog 240

<400> SEQUENCE: 242

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 243
<211> LENGTH: 39
<212> TYPE: PRT
<213> ORGANISM: Artificial Sequence
<220> FEATURE:
<223> OTHER INFORMATION: Exendin Analog 241

<400> SEQUENCE: 243

His Gly Glu Gly Thr Phe Thr Ser Asp Leu Ser Lys Gln Leu Glu Glu
1               5                   10                  15

Glu Ala Val His Leu Phe Ile Glu Trp Leu Lys Asn Gly Gly Pro Ser
            20                  25                  30

Ser Gly Ala Pro Pro Pro Ser

<210> SEQ ID NO 244
<211> LENGTH: 39
<212> TYPE: PRT
<213> ORGANISM: Artificial Sequence
<220> FEATURE:
<223> OTHER INFORMATION: Exendin Analog 242

<400> SEQUENCE: 244

His Gly Glu Gly Thr Phe Thr Ser Asp Leu Ser Lys Gln Leu Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 245
<211> LENGTH: 40
<212> TYPE: PRT
<213> ORGANISM: Artificial Sequence
<220> FEATURE:
<223> OTHER INFORMATION: Exendin Analog 243

<400> SEQUENCE: 245

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Arg
        35                  40

<210> SEQ ID NO 246
<211> LENGTH: 39
<212> TYPE: PRT
<213> ORGANISM: Artificial Sequence
<220> FEATURE:
<223> OTHER INFORMATION: Exendin Analog 244

<400> SEQUENCE: 246

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 247
<211> LENGTH: 40
<212> TYPE: PRT
<213> ORGANISM: Artificial Sequence
<220> FEATURE:
<223> OTHER INFORMATION: Exendin Analog 245

<400> SEQUENCE: 247

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

```
<210> SEQ ID NO 248
<211> LENGTH: 40
<212> TYPE: PRT
<213> ORGANISM: Artificial Sequence
<220> FEATURE:
<223> OTHER INFORMATION: Exendin Analog 246

<400> SEQUENCE: 248

His Gly Glu Gly Thr Phe Thr Ser Asp Leu Ser Lys Gln Leu Glu Glu
 1               5                  10                  15

Glu Ala Val His Leu Phe Ile Glu Trp Leu Lys Asn Gly Gly Pro Ser
            20                  25                  30

Ser Gly Ala Pro Pro Pro Ser Arg
        35                  40

<210> SEQ ID NO 249
<211> LENGTH: 39
<212> TYPE: PRT
<213> ORGANISM: Artificial Sequence
<220> FEATURE:
<223> OTHER INFORMATION: Exendin Analog 247

<400> SEQUENCE: 249

His Gly Glu Gly Thr Phe Thr Ser Asp Leu Ser Lys Gln Leu Glu Glu
 1               5                  10                  15

Glu Ala Val His Leu Phe Ile Glu Trp Leu Lys Asn Gly Gly Pro Ser
            20                  25                  30

Ser Gly Ala Pro Pro Pro Ser
        35

<210> SEQ ID NO 250
<211> LENGTH: 40
<212> TYPE: PRT
<213> ORGANISM: Artificial Sequence
<220> FEATURE:
<223> OTHER INFORMATION: Exendin Analog 248

<400> SEQUENCE: 250

His Gly Glu Gly Thr Phe Thr Ser Asp Leu Ser Lys Gln Leu Glu Glu
 1               5                  10                  15

Glu Ala Val His Leu Phe Ile Glu Trp Leu Lys Asn Gly Gly Pro Ser
            20                  25                  30

Ser Gly Ala Pro Pro Pro Ser Lys
        35                  40

<210> SEQ ID NO 251
<211> LENGTH: 40
<212> TYPE: PRT
<213> ORGANISM: Artificial Sequence
<220> FEATURE:
<223> OTHER INFORMATION: Exendin Analog 249

<400> SEQUENCE: 251

His Gly Glu Gly Thr Phe Thr Ser Asp Leu Ser Lys Gln Leu Glu Glu
 1               5                  10                  15

Glu Ala Val Lys Leu Phe Ile Glu Trp Leu Lys Asn Gly Gly Pro Ser
            20                  25                  30

Ser Gly Ala Pro Pro Pro Ser Arg
        35                  40

<210> SEQ ID NO 252
<211> LENGTH: 39
<212> TYPE: PRT
```

<213> ORGANISM: Artificial Sequence
<220> FEATURE:
<223> OTHER INFORMATION: Exendin Analog 250

<400> SEQUENCE: 252

His Gly Glu Gly Thr Phe Thr Ser Asp Leu Ser Lys Gln Leu Glu Glu
1               5                   10                  15
Glu Ala Val Lys Leu Phe Ile Glu Trp Leu Lys Asn Gly Gly Pro Ser
            20                  25                  30
Ser Gly Ala Pro Pro Pro Ser
        35

<210> SEQ ID NO 253
<211> LENGTH: 40
<212> TYPE: PRT
<213> ORGANISM: Artificial Sequence
<220> FEATURE:
<223> OTHER INFORMATION: Exendin Analog 251

<400> SEQUENCE: 253

His Gly Glu Gly Thr Phe Thr Ser Asp Leu Ser Lys Gln Leu Glu Glu
1               5                   10                  15
Glu Ala Val Lys Leu Phe Ile Glu Trp Leu Lys Asn Gly Gly Pro Ser
            20                  25                  30
Ser Gly Ala Pro Pro Pro Ser Lys
        35                  40

<210> SEQ ID NO 254
<211> LENGTH: 39
<212> TYPE: PRT
<213> ORGANISM: Artificial Sequence
<220> FEATURE:
<223> OTHER INFORMATION: Exendin Analog 252

<400> SEQUENCE: 254

His Gly Glu Gly Thr Phe Thr Ser Asp Leu Ser Lys Gln Ile Glu Glu
1               5                   10                  15
Glu Ala Val Arg Leu Phe Ile Glu Trp Leu Lys Asn Gly Gly Pro Ser
            20                  25                  30
Ser Gly Ala Pro Pro Pro Ser
        35

<210> SEQ ID NO 255
<211> LENGTH: 39
<212> TYPE: PRT
<213> ORGANISM: Artificial Sequence
<220> FEATURE:
<223> OTHER INFORMATION: Exendin Analog 253

<400> SEQUENCE: 255

His Gly Glu Gly Thr Phe Thr Ser Asp Leu Ser Lys Gln Ile Glu Glu
1               5                   10                  15
Glu Ala Val His Leu Phe Ile Glu Trp Leu Lys Asn Gly Gly Pro Ser
            20                  25                  30
Ser Gly Ala Pro Pro Pro Ser
        35

<210> SEQ ID NO 256
<211> LENGTH: 39
<212> TYPE: PRT
<213> ORGANISM: Artificial Sequence
<220> FEATURE:
<223> OTHER INFORMATION: Exendin Analog 254

<400> SEQUENCE: 256

His Gly Glu Gly Thr Phe Thr Ser Asp Leu Ser Lys Gln Ile Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
        35

<210> SEQ ID NO 257
<211> LENGTH: 40
<212> TYPE: PRT
<213> ORGANISM: Artificial Sequence
<220> FEATURE:
<223> OTHER INFORMATION: Exendin Analog 255

<400> SEQUENCE: 257

His Gly Glu Gly Thr Phe Thr Ser Asp Leu Ser Lys Gln Ile Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Arg
        35                  40

<210> SEQ ID NO 258
<211> LENGTH: 39
<212> TYPE: PRT
<213> ORGANISM: Artificial Sequence
<220> FEATURE:
<223> OTHER INFORMATION: Exendin Analog 256

<400> SEQUENCE: 258

His Gly Glu Gly Thr Phe Thr Ser Asp Leu Ser Lys Gln Ile Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 259
<211> LENGTH: 40
<212> TYPE: PRT
<213> ORGANISM: Artificial Sequence
<220> FEATURE:
<223> OTHER INFORMATION: Exendin Analog 257

<400> SEQUENCE: 259

His Gly Glu Gly Thr Phe Thr Ser Asp Leu Ser Lys Gln Ile Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys
        35                  40

<210> SEQ ID NO 260
<211> LENGTH: 40
<212> TYPE: PRT
<213> ORGANISM: Artificial Sequence
<220> FEATURE:
<223> OTHER INFORMATION: Exendin Analog 258

<400> SEQUENCE: 260

His Gly Glu Gly Thr Phe Thr Ser Asp Leu Ser Lys Gln Ile Glu Glu
1               5                   10                  15

Glu Ala Val His Leu Phe Ile Glu Trp Leu Lys Asn Gly Gly Pro Ser
            20                  25                  30

Ser Gly Ala Pro Pro Ser Arg
        35              40

<210> SEQ ID NO 261
<211> LENGTH: 39
<212> TYPE: PRT
<213> ORGANISM: Artificial Sequence
<220> FEATURE:
<223> OTHER INFORMATION: Exendin Analog 259

<400> SEQUENCE: 261

His Gly Glu Gly Thr Phe Thr Ser Asp Leu Ser Lys Gln Ile Glu Glu
1               5                   10                  15

Glu Ala Val His Leu Phe Ile Glu Trp Leu Lys Asn Gly Gly Pro Ser
            20                  25                  30

Ser Gly Ala Pro Pro Ser
        35

<210> SEQ ID NO 262
<211> LENGTH: 40
<212> TYPE: PRT
<213> ORGANISM: Artificial Sequence
<220> FEATURE:
<223> OTHER INFORMATION: Exendin Analog 260

<400> SEQUENCE: 262

His Gly Glu Gly Thr Phe Thr Ser Asp Leu Ser Lys Gln Ile Glu Glu
1               5                   10                  15

Glu Ala Val His Leu Phe Ile Glu Trp Leu Lys Asn Gly Gly Pro Ser
            20                  25                  30

Ser Gly Ala Pro Pro Ser Lys
        35              40

<210> SEQ ID NO 263
<211> LENGTH: 40
<212> TYPE: PRT
<213> ORGANISM: Artificial Sequence
<220> FEATURE:
<223> OTHER INFORMATION: Exendin Analog 261

<400> SEQUENCE: 263

His Gly Glu Gly Thr Phe Thr Ser Asp Leu Ser Lys Gln Ile Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser Arg
        35              40

<210> SEQ ID NO 264
<211> LENGTH: 39
<212> TYPE: PRT
<213> ORGANISM: Artificial Sequence
<220> FEATURE:
<223> OTHER INFORMATION: Exendin Analog 262

<400> SEQUENCE: 264

His Gly Glu Gly Thr Phe Thr Ser Asp Leu Ser Lys Gln Ile Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
        35

<210> SEQ ID NO 265
<211> LENGTH: 40
<212> TYPE: PRT
<213> ORGANISM: Artificial Sequence
<220> FEATURE:
<223> OTHER INFORMATION: Exendin Analog 263

<400> SEQUENCE: 265

His Gly Glu Gly Thr Phe Thr Ser Asp Leu Ser Lys Gln Ile Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser Lys
        35                  40

<210> SEQ ID NO 266
<211> LENGTH: 65
<212> TYPE: DNA
<213> ORGANISM: Artificial Sequence
<220> FEATURE:
<223> OTHER INFORMATION: Chemically Synthesized

<400> SEQUENCE: 266
aattccatgc acggcgaaac cttcaccagc gatctgagca acagctgga agaagaagcg      60 gttaa                                                                65

<210> SEQ ID NO 267
<211> LENGTH: 65
<212> TYPE: DNA
<213> ORGANISM: Artificial Sequence
<220> FEATURE:
<223> OTHER INFORMATION: Chemically Synthesized

<400> SEQUENCE: 267
actgttcatc gaatggctga aaaacggcgg cccgagcagc ggcccgccgc cgccgagccg      60
ttaga                                                                65

<210> SEQ ID NO 268
<211> LENGTH: 61
<212> TYPE: DNA
<213> ORGANISM: Artificial Sequence
<220> FEATURE:
<223> OTHER INFORMATION: Chemically Synthesized

<400> SEQUENCE: 268
agcttctaac ggctcggcgg cggcgcgctg ctcgggccgc cgttttttcag ccattcgatg     60 a                                                                    61

<210> SEQ ID NO 269
<211> LENGTH: 69
<212> TYPE: DNA
<213> ORGANISM: Artificial Sequence
<220> FEATURE:
<223> OTHER INFORMATION: Chemically Synthesized

```
<400> SEQUENCE: 269
acagtttaac cgcttcttct tccagctgtt tgctcagatc gctggtgaag gtgccttcgc      60
cgtgcatgg                                                             69
```